United States Patent
Li et al.

(10) Patent No.: US 10,022,701 B2
(45) Date of Patent: Jul. 17, 2018

(54) COATING METHODS USING ORGANOSILICA MATERIALS AND USES THEREOF

(71) Applicants: Quanchang Li, Dayton, NJ (US); Randall D. Partridge, Califon, NJ (US)

(72) Inventors: Quanchang Li, Dayton, NJ (US); Randall D. Partridge, Califon, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 411 days.

(21) Appl. No.: 14/966,407

(22) Filed: Dec. 11, 2015

(65) Prior Publication Data

US 2016/0167016 A1   Jun. 16, 2016

Related U.S. Application Data

(60) Provisional application No. 62/091,071, filed on Dec. 12, 2014, provisional application No. 62/091,077, filed on Dec. 12, 2014.

(51) Int. Cl.
  *B01D 53/02*      (2006.01)
  *B01J 20/26*      (2006.01)
  (Continued)

(52) U.S. Cl.
  CPC ............ *B01J 20/262* (2013.01); *B01D 15/00* (2013.01); *B01D 53/02* (2013.01); *B01D 53/04* (2013.01); *B01D 53/047* (2013.01); *B01D 53/0462* (2013.01); *B01D 67/0088* (2013.01); *B01D 69/10* (2013.01); *B01D 71/70* (2013.01); *B01J 20/0229* (2013.01); *B01J 20/0237* (2013.01); *B01J 20/06* (2013.01); *B01J 20/08* (2013.01); *B01J 20/10* (2013.01); *B01J 20/103* (2013.01); *B01J 20/16* (2013.01); *B01J 20/18* (2013.01); *B01J 20/22* (2013.01); *B01J 20/264* (2013.01); *B01J 20/286* (2013.01); *B01J 20/28011* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/3042* (2013.01); *B01J 20/3204* (2013.01); *B01J 20/3212* (2013.01); *B01J 20/3236* (2013.01); *B01J 20/3238* (2013.01); *B01J 20/3272* (2013.01); *B01J 23/44* (2013.01); *B01J 29/0308* (2013.01); *B01J 31/0274* (2013.01); *B01J 35/1019* (2013.01); *B01J 35/1023* (2013.01); *B01J 35/1028* (2013.01); *B01J 35/1061* (2013.01); *B01J 37/0213* (2013.01); *B01J 37/0236* (2013.01); *C01B 37/00* (2013.01); *C07F 7/0807* (2013.01);
  (Continued)

(58) Field of Classification Search
  CPC .... C08F 210/02; C08F 4/65916; C08F 4/027; C08F 4/64013; C08F 4/64048; C08F 4/64089; C08F 4/64148; C08F 4/64158; C08F 4/64189; C08F 4/64193; B01D 15/00; B01D 2253/20; B01D 2253/25; B01D 53/02; B01D 53/04; B01D 53/0462; B01D 53/047; B01J 20/0237; B01J 20/06; B01J 20/08; B01J 20/10; B01J 20/103; B01J 20/16; B01J 20/18; B01J 20/22; B01J 20/262; B01J 20/264
  See application file for complete search history.

(56) References Cited

U.S. PATENT DOCUMENTS 3,178,392 A   4/1965   Kriner
4,218,308 A   8/1980   Itoh et al.
(Continued)

FOREIGN PATENT DOCUMENTS

CN   101804335 A   8/2010
CN   101980013 A   2/2011
(Continued)

OTHER PUBLICATIONS

Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society; Jan. 1, 2005, pp. 60-61, vol. 127, No. 1, ACS Publications.
Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.
PCT/US2015/065208 International Search Report and Written Opinion dated May 17, 2016.
(Continued)

Primary Examiner — Christopher P Jones
(74) Attorney, Agent, or Firm — Andrew T. Ward

(57) ABSTRACT

Methods for coating a substrate with a coating including an adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the substrate and each $Z^4$ represents a hydroxyl group, a $C_1$-$C_4$ alkoxy group, a $C_1$-$C_4$ alkyl group, an oxygen atom bonded to a silicon atom of another unit or an active site on the substrate are provided. Methods of gas separation are also provided.

53 Claims, 17 Drawing Sheets

US 10,022,701 B2
Page 2

(51) Int. Cl.
*B01D 15/00* (2006.01)
*B01J 20/06* (2006.01)
*B01J 20/08* (2006.01)
*B01J 20/10* (2006.01)
*B01J 20/18* (2006.01)
*B01D 53/04* (2006.01)
*B01J 20/28* (2006.01)
*B01J 20/286* (2006.01)
*B01J 20/30* (2006.01)
*B01J 20/32* (2006.01)
*B01J 29/03* (2006.01)
*C01B 37/00* (2006.01)
*C08F 36/04* (2006.01)
*C08F 36/20* (2006.01)
*C08G 77/60* (2006.01)
*C08F 2/00* (2006.01)
*C08F 2/42* (2006.01)
*C10G 25/00* (2006.01)
*C10G 45/44* (2006.01)
*B01J 20/02* (2006.01)
*B01J 20/16* (2006.01)
*B01D 53/047* (2006.01)
*B01J 23/44* (2006.01)
*B01J 31/02* (2006.01)
*B01J 37/02* (2006.01)
*C10G 45/52* (2006.01)
*B01J 20/22* (2006.01)
*B01J 35/10* (2006.01)
*C07F 7/08* (2006.01)
*C08G 77/26* (2006.01)
*C10M 101/02* (2006.01)
*B01D 67/00* (2006.01)
*B01D 69/10* (2006.01)
*B01D 71/70* (2006.01)
*C10G 31/09* (2006.01)
*C23C 16/56* (2006.01)
*C08F 2/10* (2006.01)
*C08F 4/659* (2006.01)
*C08F 4/6592* (2006.01)

(52) U.S. Cl.
CPC .............. *C07F 7/0818* (2013.01); *C08F 2/00* (2013.01); *C08F 2/10* (2013.01); *C08F 2/42* (2013.01); *C08F 36/04* (2013.01); *C08F 36/20* (2013.01); *C08G 77/26* (2013.01); *C08G 77/60* (2013.01); *C10G 25/003* (2013.01); *C10G 31/09* (2013.01); *C10G 45/44* (2013.01); *C10G 45/52* (2013.01); *C10M 101/02* (2013.01); *C23C 16/56* (2013.01); *B01D 2253/20* (2013.01); *B01D 2253/25* (2013.01); *B01D 2256/245* (2013.01); *B01D 2257/302* (2013.01); *B01D 2257/304* (2013.01); *B01D 2257/40* (2013.01); *B01D 2257/504* (2013.01); *B01D 2257/80* (2013.01); *B01J 2220/86* (2013.01); *C08F 4/659* (2013.01); *C08F 4/65912* (2013.01); *C08F 4/65916* (2013.01); *C08F 4/65925* (2013.01); *C08F 4/65927* (2013.01)

(56) References Cited

U.S. PATENT DOCUMENTS

| | | | |
|---|---|---|---|
| 5,630,937 A | 5/1997 | Betz et al. |
| 5,719,322 A | 2/1998 | Lansbarkis et al. |
| 7,300,905 B2 | 11/2007 | Keefer et al. |
| 7,497,965 B2 | 3/2009 | Wariishi et al. |
| 7,538,065 B2 | 5/2009 | McCarthy et al. |
| 7,682,502 B2 | 3/2010 | McCarthy et al. |
| 7,705,062 B2 | 4/2010 | Markowitz et al. |
| 7,754,330 B2 | 7/2010 | Hamada et al. |
| 7,767,620 B2 | 8/2010 | Whitnall et al. |
| 7,947,799 B2 | 5/2011 | Landskron et al. |
| 8,110,692 B2 | 2/2012 | Bellussi et al. |
| 8,211,498 B2 | 7/2012 | Ku et al. |
| 8,277,600 B2 | 10/2012 | Hamada et al. |
| 8,277,661 B2 | 10/2012 | Sah et al. |
| 8,425,762 B2 | 4/2013 | McCarthy et al. |
| 8,441,006 B2 | 5/2013 | Mchalak et al. |
| 8,470,074 B2 | 6/2013 | Baugh et al. |
| 8,524,624 B2 * | 9/2013 | Garcia-Martinez ...... B01J 20/18 423/700 |
| 8,545,694 B2 | 10/2013 | McCarthy et al. |
| 8,562,856 B2 | 10/2013 | Giannantonio et al. |
| 8,568,520 B2 | 10/2013 | Ohashi et al. |
| 8,598,070 B1 | 12/2013 | Baugh et al. |
| 8,598,071 B1 | 12/2013 | Baugh et al. |
| 8,809,561 B2 | 8/2014 | Bellussi et al. |
| 9,181,282 B2 | 11/2015 | Ide et al. |
| 2003/0188991 A1 | 10/2003 | Shan et al. |
| 2005/0093189 A1 | 5/2005 | Vo |
| 2006/0058565 A1 | 3/2006 | DeWild |
| 2006/0070917 A1 | 4/2006 | McCarthy et al. |
| 2006/0165574 A1 | 7/2006 | Sayari |
| 2007/0034992 A1 | 2/2007 | Wariishi et al. |
| 2007/0054136 A1 | 3/2007 | Takahashi et al. |
| 2007/0112242 A1 | 5/2007 | Edmiston |
| 2007/0173401 A1 | 7/2007 | Landskron et al. |
| 2008/0276804 A1 * | 11/2008 | Sayari .................. B01D 53/02 95/285 |
| 2009/0130412 A1 | 5/2009 | Hatton et al. |
| 2009/0215612 A1 | 8/2009 | McCarthy et al. |
| 2009/0294922 A1 | 12/2009 | Hamada et al. |
| 2010/0155302 A1 | 6/2010 | Kaminsky et al. |
| 2010/0233482 A1 | 9/2010 | Hamada et al. |
| 2011/0139685 A1 | 6/2011 | McCarthy et al. |
| 2011/0248214 A1 * | 10/2011 | MacLachlan ...... B01D 67/0048 252/299.01 |
| 2012/0032111 A1 * | 2/2012 | Edmiston .................. B09C 1/08 252/184 |
| 2012/0059181 A1 | 3/2012 | Bellussi et al. |
| 2012/0160742 A1 | 6/2012 | Sohn et al. |
| 2013/0075876 A1 | 3/2013 | Goethals et al. |
| 2013/0078172 A1 | 3/2013 | Li et al. |
| 2013/0249049 A1 | 9/2013 | Michalak et al. |
| 2014/0004358 A1 | 1/2014 | Blackwell et al. |
| 2014/0186246 A1 | 7/2014 | Calabro et al. |
| 2014/0208753 A1 | 7/2014 | Liu et al. |
| 2015/0011787 A1 | 1/2015 | Bellussi et al. |
| 2016/0229959 A1 * | 8/2016 | Li ........................ B01D 53/02 |

FOREIGN PATENT DOCUMENTS

| | | |
|---|---|---|
| CN | 102052713 A | 5/2011 |
| CN | 102643429 A | 8/2012 |
| CN | 103157362 A | 6/2013 |
| CN | 103495340 A | 1/2014 |
| CN | 103613975 A | 3/2014 |
| CN | 104117343 A | 10/2014 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |

(56) References Cited

FOREIGN PATENT DOCUMENTS

| RU | 2291878 C1 | 1/2007 |
|---|---|---|
| WO | 9610537 A1 | 4/1996 |
| WO | 2006032140 A1 | 3/2006 |
| WO | 2007081212 A1 | 7/2007 |
| WO | 2011145933 A1 | 11/2011 |
| WO | 2013093022 A1 | 6/2013 |
| WO | 2014010512 A1 | 1/2014 |
| WO | 2014090757 A1 | 6/2014 |

OTHER PUBLICATIONS

PCT/US2015/065200 Partial International Search Report and Written Opinion dated May 23, 2016.
Diaz et al, "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic siliconmethylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.
Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.
Melde et al., "Mesoporous Sieves with Unified Hybrid Inorganic/Organic Frameworks", Chemistry of Materials, Oct. 9, 1999, pp. 3302-3308, vol. 11.

Eliseeva et al., "Antifoaming additive for alkaline absorption solutions for removal of carbon dioxide from synthesis gas", Khimicheskaya Promyshlennost, 1999, pp. 632-633, vol. 10.
Brondani, et al., "Polyfunctional carbosilanes and organosilicon compounds. Synthesis via Grignard reactions", Tetrahedron Letters, Mar. 2, 2001, pp. 2111-2114, vol. 34.
Gilman et al., "Reactions of triphenylsilyllithium with some dichloropropenes", Journal of Organometallic Chemistry, Apr. 13, 2001, pp. 293-303, vol. 2.
Landskron et al., "Periodic Mesoporous Organosilicas Containing Interconnected [Si(CH2)]3 Rings", Science, Oct. 10, 2003, pp. 266-269, vol. 302.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.

* cited by examiner

Fig. 9a
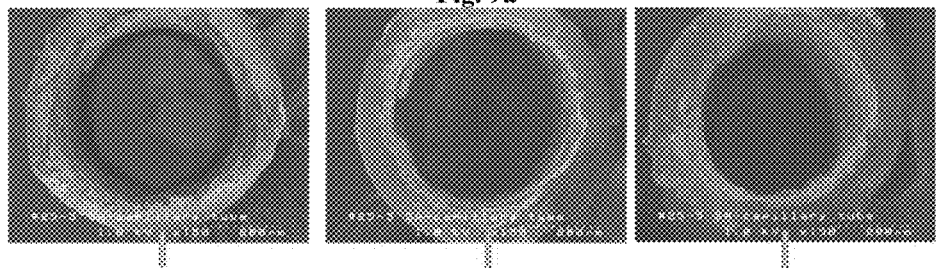
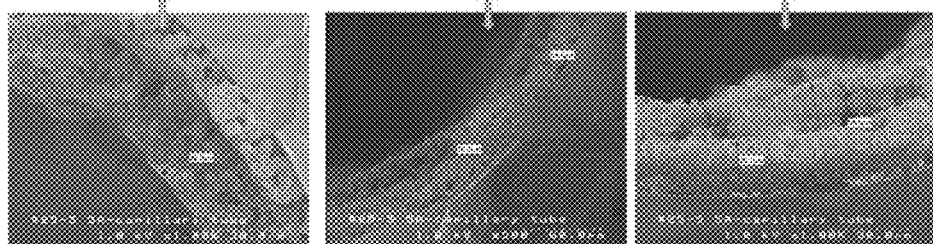
Fig. 9b

Fig. 10a
Fig. 10b
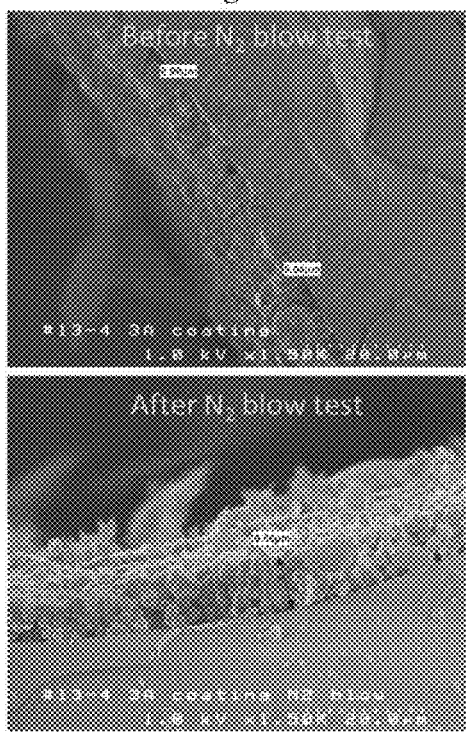
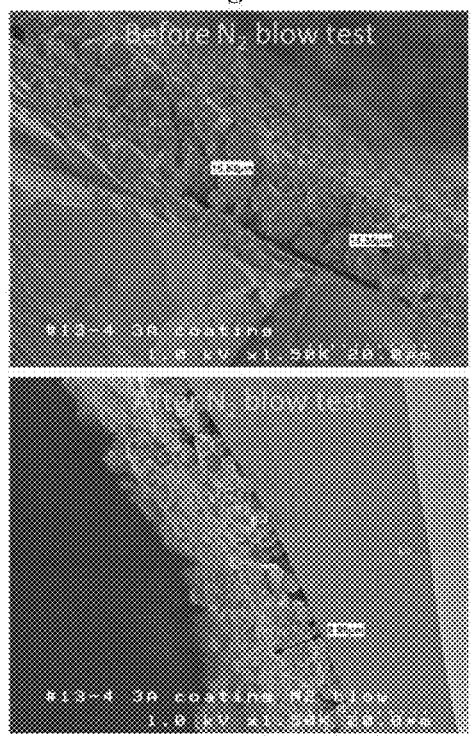
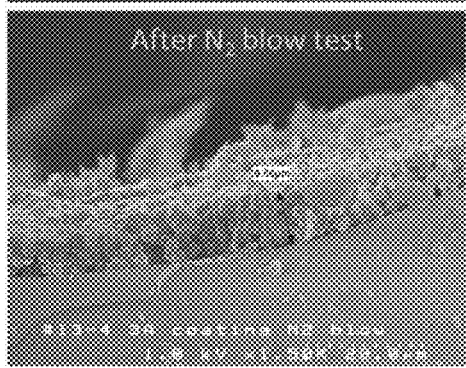
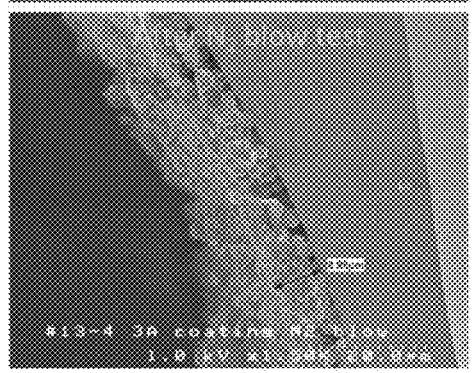
Fig. 10c
Fig. 10d

Fig. 11a
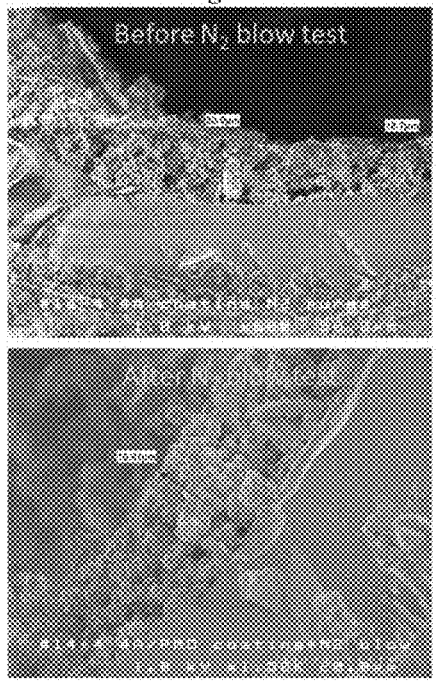
Fig. 11c
Fig. 11b
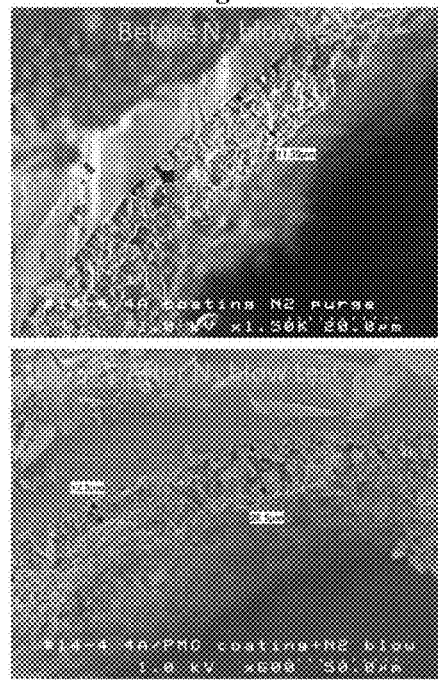
Fig. 11d

US 10,022,701 B2

COATING METHODS USING ORGANOSILICA MATERIALS AND USES THEREOF

CROSS-REFERENCE TO RELATED APPLICATIONS

This application claims priority to U.S. Provisional Application Ser. No. 62/091,071 filed Dec. 12, 2014 and U.S. Provisional Application Ser. No. 62/091,077 filed Dec. 12, 2014, which are herein incorporated by reference in their entirety.

This application is also related to several other co-pending U.S. applications, filed on even date herewith and bearing application Ser. Nos. 14/965,992 (entitled "Organosilica Materials and Uses Thereof"), 14/966,001 (entitled "Methods of Producing Organosilica Materials and Uses Thereof"), 14/966,071 (entitled "Aromatic Hydrogenation Catalysts and Uses Thereof"), 14/965,984 (entitled "Organosilica Materials and Uses Thereof"), 14/966,383 (entitled "Organosilica Materials and Uses Thereof"), 14/966,015 (entitled "Organosilica Materials and Uses Thereof"), 14/966,284 (entitled "Organosilica Materials and Uses Thereof"), 14/966,445 (entitled "Membrane Fabrication Method Using Organosilica Materials and Uses Thereof"), 14/966,534 (entitled "Adsorbent for Heteroatom Species Removal and Uses Thereof"), and 14/966,790 (entitled "Method for Separating Aromatic Compounds from Lube Basestocks"), the entire disclosures of each of which are incorporated by reference herein.

Additionally, this application is further related to several other co-pending U.S. applications bearing application Ser. Nos. 15/526,512 (entitled "Organosilica Materials for Use as Adsorbents for Oxygenate Removal"), 15/526,524 (entitled "Supported Catalyst for Olefin Polymerization"), 15/526,529 (entitled "Supported Catalyst for Olefin Polymerization"), 15/526,513 (entitled "Supported Catalyst for Olefin Polymerization"), and 15/526,521 (entitled "Supported Catalyst for Olefin Polymerization"), the entire disclosures of each of which are incorporated by reference herein.

FIELD OF THE INVENTION

The present invention relates to methods of coating adsorbent material using organosilica materials as a binder and processes for gas and liquid separation.

BACKGROUND OF THE INVENTION

Gas separation is important in many industries for removing undesirable contaminants from a gas stream and for achieving a desired gas composition. For example, natural gas from many gas fields can contain significant levels of $H_2O$, $SO_2$, $H_2S$, $CO_2$, $N_2$, mercaptans, and/or heavy hydrocarbons that have to be removed to various degrees before the gas can be transported to market. It is preferred that as much of the acid gases (e.g., $H_2S$ and $CO_2$) be removed from natural gas as possible to leave methane as the recovered component. Small increases in recovery of methane can result in significant improvements in process economics and also serve to prevent unwanted resource loss. It is desirable to recover more than 80 vol %, preferably more than 90 vol %, of the methane when detrimental impurities are removed.

Additionally, synthesis gas (syngas) typically requires removal and separation of various components before it can be used in fuel, chemical and power applications because all of these applications have a specification of the exact composition of the syngas required for the process. As produced, syngas can contain at least CO and $H_2$. Other molecular components in syngas can be $CH_4$, $CO_2$, $H_2S$, $H_2O$, $N_2$, and combinations thereof. Minority (or trace) components in the gas can include hydrocarbons, $NH_3$, $NO_x$, and the like, and combinations thereof. In almost all applications, most of the $H_2S$ should typically be removed from the syngas before it can be used, and, in many applications, it can be desirable to remove much of the $CO_2$.

Adsorptive gas separation techniques are common in various industries using solid sorbent materials such as activated charcoal or a porous solid oxide such as alumina, silica-alumina, silica, or a crystalline zeolite. Adsorptive separation may be achieved by equilibrium or kinetic mechanisms. A large majority of processes operate through the equilibrium adsorption of the gas mixture where the adsorptive selectivity is primarily based upon differential equilibrium uptake of one or more species based on parameters such as pore size of the adsorbent. Kinetically based separation involves differences in the diffusion rates of different components of the gas mixture and allows different species to be separated regardless of similar equilibrium adsorption parameters.

Adsorptive separation processes may use packed beds of adsorbent particulates or a structured adsorbent bed, such as a monolith, either in the form of one single block or in the form of extrudates with multiple channels or cells, such as a honeycomb structured monolith. In order to prepare structured adsorbent beds (e.g., monolith) for use in gas separation processes, the beds may be coated with the adsorbent material (e.g., zeolites). However, uniform adsorbent coating is difficult to achieve as well as maintained integrity of the coating during use in gas separation processes, such as pressure swing adsorption (PSA) where high gas velocities can result in degradation of the adsorbent coating. Thus, there is a need for methods of coating adsorbent materials that result in uniform adsorbent coatings which can maintain physical integrity through various separation processes.

Porous inorganic solids have found great utility as separation media for industrial application. In particular, mesoporous materials, such as silicas and aluminas, having a periodic arrangement of mesopores are attractive materials for use in adsorption and separation processes due to their uniform and tunable pores, high surface areas and large pore volumes. Such mesoporous materials are known to have large specific surface areas (e.g., 1000 m²/g) and large pore volumes (e.g., 1 cm³/g). For these reasons, such mesoporous materials enable molecules to rapidly diffuse into the pores. Consequently, such mesoporous materials can be useful as large capacity adsorbents. Additionally, such mesoporous organosilicas may be used as a binder along with other adsorbent materials (e.g., zeolites) to form an adsorbent coating for separation processes.

However, mesoporous organosilicas, which may be used as adsorbents and/or binders are conventionally formed by the self-assembly of the silsesquioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science*, 302:266-269 (2003)] report the self-assembly of 1,3,5-tris[diethoxysila]cylcohexane [(EtO)$_2$SiCH$_2$]$_3$ in the presence of a base and the structure directing agent, cetyltrimethylammonium bromide to form PMOs that are bridged organosilicas with a periodic mesoporous framework, which consist of $SiO_3R$ or $SiO_2R_2$ building blocks, where R is a bridging organic group. In PMOs, the organic groups can be homogenously distributed in the pore walls. U.S. Pat. Pub. No. 2012/0059181 reports the preparation of a crystalline hybrid organic-inorganic silicate formed from 1,1,3,3,5,5 hexaethoxy-1,3,5 trisilyl cyclohexane in the presence of $NaAlO_2$ and base. U.S. Patent Application Publication No. 2007/003492 reports preparation of a composition formed from 1,1,3,3,5,5 hexaethoxy-1,3,5 trisilyl cyclohexane in the presence of propylene glycol monomethyl ether.

However, the use of a structure directing agent, such as a surfactant, in the preparation of an organosilica material, requires a complicated, energy intensive process to eliminate the structure directing agent at the end of the preparation process. For example, calcining may be required as well as wastewater disposal steps and associated costs to dispose of the structure directing agent. This limits the ability to scale-up the process for industrial applications.

Therefore, there is a need for improved methods of coating adsorbent materials for gas separation processes using organosilica materials that can be prepared by a method that can be practiced in the absence of a structure directing agent, a porogen or surfactant.

SUMMARY OF THE INVENTION

It has been found that substrates can be successfully coated with adsorbent materials and an organosilica material binder without the need for a structure directing agent, a porogen or surfactant.

Thus, in one aspect, embodiments of the invention provide a method for coating a substrate, the method comprising: adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen atom bonded to a silicon atom of another compound and each $Z^2$ represents, a hydroxyl group, a $C_1$-$C_4$ alkoxy group, a $C_1$-$C_4$ alkyl group or an oxygen atom bonded to a silicon atom of another compound; adding an adsorbent material to the solution to form a slurry; coating the slurry onto a substrate; aging the slurry; and drying the slurry to obtain a coating comprising the adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the substrate and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

In still another aspect, embodiments of the invention provide an organosilica material-coated substrate made according to the methods described herein.

In still another aspect, embodiments of the invention provide a gas separation process comprising contacting a gas mixture comprising $CH_4$ and at least one contaminant selected from the group consisting $CO_2$, $H_2O$, $H_2S$, $NO_x$, and $SO_x$ with the organosilica material-coated substrate as described herein.

Other embodiments, including particular aspects of the embodiments summarized above, will be evident from the detailed description that follows.

BRIEF DESCRIPTION OF THE DRAWINGS

FIG. 9a (top row) illustrates SEM images of a cross-section of Coating 9 on a capillary column.

FIG. 9b (bottom row) illustrates SEM images of a more magnified view of a cross-section of Coating 9 on a capillary column that correlates to each image above in FIG. 9a.

FIGS. 10a and 10b illustrate SEM images of a cross-section of Coating 2 on a capillary column before a high velocity $N_2$ purge.

FIGS. 10c and 10d illustrate SEM images of a cross-section of Coating 2 on a capillary column after a high velocity $N_2$ purge.

FIGS. 11a and 11b illustrate SEM images of a cross-section of Coating 3 on a capillary column before a high velocity $N_2$ purge.

FIGS. 11c and 11d illustrate SEM images of a cross-section of Coating 3 on a capillary column after a high velocity $N_2$ purge.

FIG. 13c illustrates SEM images of a more magnified view of a cross-section of Coating 10 on a SiO₂/Si wafer.

DETAILED DESCRIPTION OF THE INVENTION

Figure 1A:
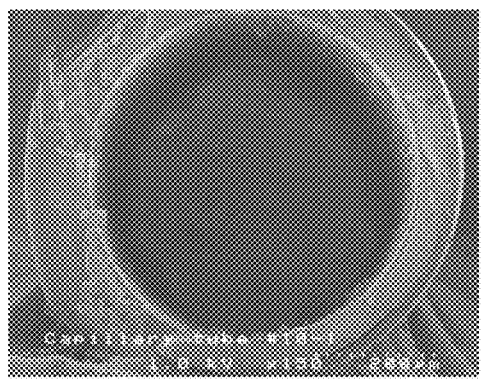
FIG. 1a illustrates a scanning electron microscope (SEM) image of a cross-section of Coating 1 on a capillary column.

In various aspects of the invention, methods for coating a substrate, organosilica material-coated substrates and gas and separation processes using the organosilica material-coated substrates are provided.

I. DEFINITIONS

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$," means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—CH₃), "$C_2$ alkyl" refers to ethyl (—CH₂CH₃), "$C_3$ alkyl" refers to propyl (—CH₂CH₂CH₃) and "$C_4$ alkyl" refers to butyl (e.g. —CH₂CH₂CH₂CH₃, —(CH₃)CHCH₂CH₃, —CH₂CH (CH₃)₂, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —CH₂—, —CH₂CH₂—, —CH(CH₃)CH₂—, —CH₂CH₂CH₂—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

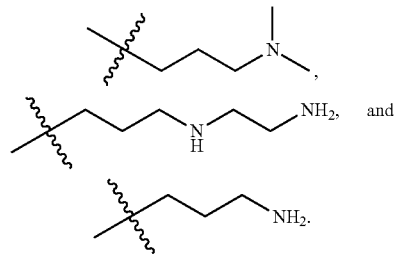

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

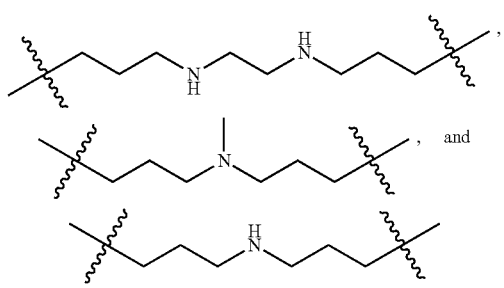

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH=CH—, —CH$_2$CH$_2$CH=CHCH$_2$—, etc. —CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompasses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. —CH$_2$CH$_2$—, —CH(CH$_3$)CH$_2$—, —CH$_2$CH$_2$CH$_2$—, etc. The alkynylene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. METHODS FOR COATING A SUBSTRATE

The invention relates to methods for coating a substrate, the method comprising:

(a) adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen atom bonded to a silicon atom of another compound and each $Z^2$ represents, a hydroxyl group, a $C_1$-$C_4$ alkoxy group, a $C_1$-$C_4$ alkyl group or an oxygen atom bonded to a silicon atom of another compound;

(b) adding an adsorbent material to the solution to form a slurry;

(c) coating the slurry onto a substrate;

(d) aging the slurry; and (e) drying the slurry to obtain a coating comprising the adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the substrate and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

As used herein, and unless otherwise specified, "an oxygen atom bonded to a silicon atom of another unit or an active site on the substrate" means that the oxygen atom can advantageously displace a moiety (particularly an oxygen-containing moiety such as a hydroxyl, an alkoxy or the like), if present, on a silicon atom of another unit or a moiety (particularly an oxygen-containing moiety such as a hydroxyl, an alkoxy or the like), if present, on an active site of the substrate so the oxygen atom may be bonded directly to the silicon atom of another unit thereby connecting the two units, e.g., via a Si—O—Si linkage or the oxygen atom may be bonded directly to the active site on the substrate thereby connecting the unit to the substrate. As used herein, and unless otherwise specified, "a bond to a silicon atom of another unit or an active site on the substrate" means that the bond can advantageously displace a moiety (particularly an oxygen-containing moiety such as a hydroxyl, an alkoxy or the like), if present, on a silicon atom of another unit or a moiety (particularly an oxygen-containing moiety such as a hydroxyl, an alkoxy or the like), if present, on an active site of the substrate so there may be a bond directly to the silicon atom of another unit thereby connecting the two units, e.g., via a Si—O—Si linkage or a bond directly to the active site on the substrate thereby connecting the unit to the substrate. For clarity, in this bonding scenario, the "another unit" can be a unit of the same type or a unit of a different type. Active sites on a substrate can include, but are not limited to Ti atoms, Si atoms, Zr atoms, and combinations thereof. Any metal oxide surface can be an active site. Additionally or alternatively, it understood herein, that other heteroatoms (e.g., N, S) in addition to oxygen may be bridge the Si atoms of the polymer to the active sites of the substrate.

II.A. Aqueous Mixture

The aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. As used herein, porogen does not include water. An example of a porogen is a block copolymer (e.g., a di-block polymer). Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or from about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, from about 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, about 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

II.B. Compounds of Formula (Ia)

The methods provided herein comprise the step of adding at least one compound of Formula $[Z^1Z^2SiCH_2]_3$ (Ia) into the aqueous mixture to form a solution, wherein each $Z^1$ can be a hydroxyl group, a $C_1$-$C_4$ alkoxy group, or an oxygen atom bonded to a silicon atom of another compound and each $Z^2$ can be a hydroxyl group, a $C_1$-$C_4$ alkoxy group or a $C_1$-$C_4$ alkyl group, or an oxygen atom bonded to a silicon atom of another compound.

As used herein, and unless otherwise specified, "a bond to a silicon atom of another compound" means the bond can advantageously displace a moiety (particularly an oxygen-containing moiety such as a hydroxyl, an alkoxy or the like), if present, on a silicon atom of the another compound so there may be a bond directly to the silicon atom of the another compound thereby connecting the two compounds, e.g., via a Si—O—Si linkage. As used herein, and unless otherwise specified, "an oxygen atom bonded to a silicon atom of another compound" means that the oxygen atom can advantageously displace a moiety (particularly an oxygen-containing moiety such as a hydroxyl, if present, on a silicon atom of the another compound so the oxygen atom may be bonded directly to the silicon atom of the another compound thereby connecting the two compounds, e.g., via a Si—O—Si linkage. For clarity, in these bonding scenarios, the "another compound" can be a compound of the same type or a compound of a different type.

In one embodiment, each $Z^1$ can be a hydroxyl group.

Additionally or alternatively, each $Z^1$ can comprise a $C_1$-$C_3$ alkoxy or methoxy or ethoxy.

Additionally or alternatively, each $Z^1$ can be a hydroxyl group or a $C_1$-$C_2$ alkoxy group.

Additionally or alternatively, each $Z^1$ can be an oxygen atom bonded to a silicon atom of another compound.

Additionally or alternatively, each $Z^1$ can be a hydroxyl group, a $C_1$-$C_2$ alkoxy group or an oxygen atom bonded to a silicon atom of another compound.

Additionally or alternatively, each $Z^2$ can be a hydroxyl group.

Additionally or alternatively, each $Z^2$ can comprise a $C_1$-$C_4$ alkoxy, a $C_1$-$C_3$ alkoxy or methoxy or ethoxy. Additionally or alternatively, each $Z^2$ can comprise methyl, ethyl or propyl, such as a methyl or ethyl.

Additionally or alternatively, each $Z^2$ can be a hydroxyl group, a $C_1$-$C_2$ alkoxy group or a $C_1$-$C_2$ alkyl group.

Additionally or alternatively, each $Z^1$ can be an oxygen atom bonded to a silicon atom of another compound.

Additionally or alternatively, each $Z^2$ can be a hydroxyl group, a $C_1$-$C_2$ alkoxy group, a $C_1$-$C_2$ alkyl group or an oxygen atom bonded to a silicon atom of another compound.

Additionally or alternatively, each $Z^1$ can be a hydroxyl group, a $C_1$-$C_2$ alkoxy group or an oxygen atom bonded to a silicon atom of another compound and each $Z^2$ can be a hydroxyl group, a $C_1$-$C_2$ alkoxy group, a $C_1$-$C_2$ alkyl group or an oxygen atom bonded to a silicon atom of another compound.

Additionally or alternatively, each $Z^1$ can a $C_1$-$C_2$ alkoxy group and each $Z^2$ can be a $C_1$-$C_2$ alkoxy group or a $C_1$-$C_2$ alkyl group.

Additionally or alternatively, each $Z^1$ can be hydroxyl, methoxy, ethoxy or an oxygen atom bonded to a silicon atom of another compound and each $Z^2$ can be methyl or ethyl.

In a particular embodiment, each $Z^1$ and each $Z^2$ can be ethoxy, such that the compound corresponding to Formula (Ia) can be 1,1,3,3,5,5-hexaethoxy-1,3,5-trisilacyclohexane, $[(EtO)_2SiCH_2]_3$.

In a particular embodiment, each $Z^1$ can be ethoxy and each $Z^2$ can be methyl, such that compound corresponding to Formula (Ia) can be 1,3,5-trimethyl-1,3,5-triethoxy-1,3,5-trisilacyclohexane, $[EtOCH_3SiCH_2]_3$.

In various aspects, more than one compound of Formula (Ia) (e.g., same or different compound) may be added to the aqueous mixture to form a solution. For example, $[(EtO)_2SiCH_2]_3$ and $[EtOCH_3SiCH_2]_3$ may both be added to the aqueous mixture to form a solution.

In various aspects, more than one compound of Formula (Ia) (e.g., same or different compound) may be added to the aqueous mixture to form a solution. For example, $[(EtO)_2SiCH_2]_3$ and $[EtOCH_3SiCH_2]_3$ may both be added to the aqueous mixture to form a solution.

When more than one compound of Formula (Ia) is used, the respective compounds may be used in a wide variety of molar ratios. For example, if two compounds of Formula (Ia) are used, the molar ratio of each compound may vary from 1:99 to 99:1, such as from 10:90 to 90:10. The use of different compounds of Formula (Ia) allows to tailor the properties of the organosilica materials made by the process of the invention, as will be further explained in the examples and in the section of this specification describing the properties of the organosilicas made by the present processes.

II.C. Compounds of Formula (II)

In additional embodiments, the methods provided herein can further comprise adding to the aqueous solution a compound of Formula $R^1OR^2R^3R^4Si$ (II), wherein each $R^1$ can be a hydrogen atom, a $C_1$-$C_6$ alkyl group or a bond to a silicon atom of another compound, and $R^2$, $R^3$ and $R^4$ each independently can be selected from the group consisting of a hydrogen atom, a $C_1$-$C_6$ alkyl group, a $C_1$-$C_6$ alkoxy group, a nitrogen-containing $C_1$-$C_{10}$ alkyl group, a nitrogen-containing heteroaralkyl group, a nitrogen-containing optionally substituted heterocycloalkyl group, and an oxygen atom bonded to a silicon atom of another compound.

In one embodiment, $R^1$ can be a hydrogen atom.

Additionally or alternatively, each $R^1$ can be a $C_1$-$C_5$ alkyl group, a $C_1$-$C_4$ alkyl group, a $C_1$-$C_3$ alkyl group, a $C_1$-$C_2$ alkyl group, or methyl. In particular, each $R^1$ can be methyl or ethyl.

Additionally or alternatively, each $R^1$ can be a bond to a silicon atom of another compound Additionally or alternatively, $R^2$, $R^3$ and $R^4$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $R^1$ can be a $C_1$-$C_2$ alkyl group and $R^2$, $R^3$ and $R^4$ can be each independently a $C_1$-$C_2$ alkyl group.

Additionally or alternatively, $R^2$, $R^3$ and $R^4$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $R^1$ can be a $C_1$-$C_2$ alkyl group and $R^2$, $R^3$ and $R^4$ can be each independently a $C_1$-$C_2$ alkoxy group.

Additionally or alternatively, each $R^1$ can be a $C_1$-$C_2$ alkyl group and $R^2$, $R^3$ and $R^4$ can be each independently a $C_1$-$C_2$ alkyl group or a $C_1$-$C_2$ alkoxy group.

Additionally or alternatively, $R^2$, $R^3$ and $R^4$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $R^2$, $R^3$ and $R^4$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

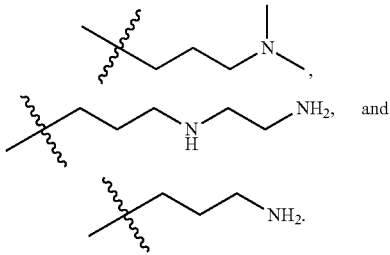

Additionally or alternatively, each $R^1$ can be a $C_1$-$C_2$ alkyl group and $R^2$, $R^3$ and $R^4$ can be each independently a nitrogen-containing $C_3$-$C_8$ alkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group or a nitrogen-containing $C_3$-$C_8$ alkyl group.

Additionally or alternatively, $R^2$, $R^3$ and $R^4$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $R^1$ can be a $C_1$-$C_2$ alkyl group and $R^2$, $R^3$ and $R^4$ can be each independently a nitrogen-containing heteroaralkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $R^2$, $R^3$ and $R^4$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $R^1$ can be a $C_1$-$C_2$ alkyl group and $R^2$, $R^3$ and $R^4$ can be each independently a nitrogen-containing optionally substituted heterocycloalkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, $R^2$, $R^3$ and $R^4$ can be each independently an oxygen atom bonded to a silicon atom of another compound.

Additionally or alternatively, each $R^1$ can be a hydrogen atom, a $C_1$-$C_2$ alkyl group or a bond to a silicon atom of another compound and $R^2$, $R^3$ and $R^4$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, a nitrogen-containing optionally substituted $C_4$-$C_{10}$ heterocycloalkyl group, or an oxygen atom bonded to a silicon atom of another compound.

Additionally or alternatively, each $R^1$ can be a $C_1$-$C_2$ alkyl group and $R^2$, $R^3$ and $R^4$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group In a particular embodiment, each $R^1$ can be ethyl and each $R^2$, $R^3$ and $R^4$ can be ethoxy, such that the compound corresponding to Formula (II) can be tetraethyl orthosilicate (TEOS) ($(EtO)_4Si$).

In another particular embodiment, each $R^1$ can be ethyl, each $R^2$ can be methyl and each $R^3$ and $R^4$ can be ethoxy, such that the compound corresponding to Formula (II) can be methyltriethoxysilane (MTES) ($(EtO)_3CH_3Si$).

In another particular embodiment, each $R^1$ can be ethyl, each $R^2$ and $R^3$ can be ethoxy and each $R^4$ can be

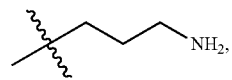 [SMILES: *CCCN]

such that the compound corresponding to Formula (II) can be (3-aminopropyl)triethoxysilane ($H_2N(CH_2)_3(EtO)_3Si$).

In another particular embodiment, each $R^1$ can be methyl, each $R^2$ and $R^3$ can be methoxy and each $R^4$ can be

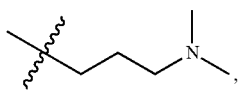 [SMILES: *CCCN(C)C]

such that the compound corresponding to Formula (II) can be (N,N-dimethylaminopropyl)trimethoxysilane $(((CH_3)_2N(CH_2)_3)(MeO)_3Si)$.

In another particular embodiment, each $R^1$ can be ethyl, each $R^2$ and $R^3$ can be ethoxy and each $R^4$ can be

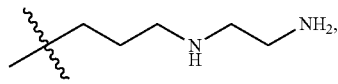 [SMILES: *CCCNCCN]

such that the compound corresponding to Formula (II) can be (N-(2-aminoethyl)-3-aminopropyltriethoxysilane $((H_2N(CH_2)_2NH(CH_2)_3)(EtO)_3Si)$.

In another particular embodiment, each $R^1$ can be ethyl, each $R^2$ and $R^3$ can be ethoxy and each $R^4$ can be

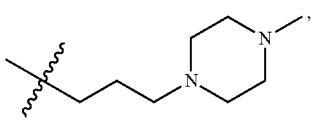 [SMILES: *CCCN1CCN(C)CC1]

such that the compound corresponding to Formula (II) can be 4-methyl-1-(3-triethoxysilylpropyl)-piperazine.

In another particular embodiment, each $R^1$ can be ethyl, each $R^2$ and $R^3$ can be ethoxy and each $R^4$ can be

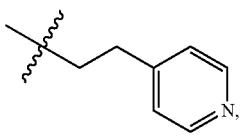 [SMILES: *CCc1ccncc1]

such that the compound corresponding to Formula (II) can be 4-(2-(triethoxysilyl)ethyl)pyridine.

In another particular embodiment, each $R^1$ can be ethyl, each $R^2$ and $R^3$ can be ethoxy and $R^4$ can be

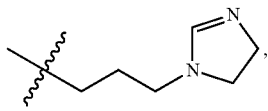

such that the compound corresponding to Formula (II) can be 1-(3-(triethoxysilyl)propyl)-4,5-dihydro-1H-imidazole.

The molar ratio of compound of Formula (Ia) to compound of Formula (II) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (II) can be from about 4:1 to about 1:4 or from about 2.5:1 to about 1:2.5, about 2:1 to about 1:2, such as about 1.5:1 to about 1.5:1.

II.D. Compounds of Formula (III)

In additional embodiments, the methods provided herein can further comprise adding to the aqueous solution a compound of Formula $Z^5Z^6Z^7Si-R-Si\ Z^5Z^6Z^7$ (III), wherein each $Z^5$ independently can be a hydroxyl group, a $C_1$-$C_4$ alkoxy group or an oxygen atom bonded to a silicon atom of another compound; each $Z^6$ and $Z^7$ independently can be a hydroxyl group, a $C_1$-$C_4$ alkoxy group, a $C_1$-$C_4$ alkyl group or an oxygen atom bonded to a silicon atom of another compound; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl group, and an optionally substituted $C_4$-$C_{20}$ heterocycloalkyl group.

In one embodiment, each $Z^5$ can be a hydroxyl group.

Additionally or alternatively, each $Z^5$ can be a $C_1$-$C_3$ alkoxy group, a $C_1$-$C_2$ alkoxy group, or methoxy.

Additionally or alternatively, each $Z^5$ can be an oxygen atom bonded to a silicon atom of another compound.

Additionally or alternatively, each $Z^6$ and $Z^7$ independently can be a hydroxyl group.

Additionally or alternatively, each $Z^6$ and $Z^7$ independently can be a $C_1$-$C_3$ alkoxy group, a $C_1$-$C_2$ alkoxy group, or methoxy.

Additionally or alternatively, each $Z^5$ can be a $C_1$-$C_2$ alkoxy group and each $Z^6$ and $Z^7$ independently can be a $C_1$-$C_2$ alkoxy group.

Additionally or alternatively, each $Z^6$ and $Z^7$ independently can be a $C_1$-$C_3$ alkyl group, a $C_1$-$C_2$ alkyl group, or methyl.

Additionally or alternatively, each $Z^5$ can be a $C_1$-$C_2$ alkoxy group and each $Z^6$ and $Z^7$ independently can be a $C_1$-$C_2$ alkyl group.

Additionally or alternatively, each $Z^6$ and $Z^7$ independently can be an oxygen atom bonded to a silicon atom of another compound.

Additionally or alternatively, each $Z^5$ can be a hydroxyl group, a $C_1$-$C_2$ alkoxy group or an oxygen atom bonded to a silicon atom of another compound and each $Z^6$ and $Z^7$ independently can be a hydroxyl group, a $C_1$-$C_2$ alkoxy group, a $C_1$-$C_2$ alkyl group or an oxygen atom bonded to a silicon atom of another compound.

Additionally or alternatively, each $Z^5$ can be a $C_1$-$C_2$ alkoxy group and each $Z^6$ and $Z^7$ independently can be a $C_1$-$C_2$ alkoxy group or a $C_1$-$C_2$ alkyl group.

Additionally or alternatively, each R can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkylene group.

Additionally or alternatively, each R can be a $C_2$-$C_7$ alkenylene group, a $C_1$-$C_6$ alkenylene group, a $C_2$-$C_5$ alkenylene group, a $C_2$-$C_4$ a alkenylene group, a $C_2$-$C_3$ alkenylene group, or —CH═CH—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkenylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkylene group or a $C_1$-$C_2$ alkenylene group.

Additionally or alternatively, each R can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkynylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group or a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

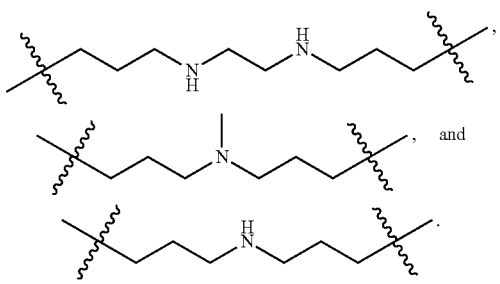

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a nitrogen-containing $C_4$-$C_{10}$ alkylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be an optionally substituted $C_6$-$C_{10}$ aralkyl.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, or an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinyl-ethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be an optionally substituted $C_4$-$C_{12}$ heterocycloalkyl group.

Additionally or alternatively, each $Z^5$ can be a hydroxyl group, a $C_1$-$C_2$ alkoxy group or an oxygen atom bonded to a silicon atom or another compound; each $Z^6$ and $Z^7$ independently can be a hydroxyl group, a $C_1$-$C_2$ alkoxy group or a $C_1$-$C_2$ alkyl group or an oxygen atom bonded to a silicon atom or another compound; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl, or an optionally substituted $C_4$-$C_{12}$ heterocycloalkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl, or an optionally substituted $C_4$-$C_{12}$ heterocycloalkyl group.

In a particular embodiment, each $Z^5$ and $Z^6$ can be ethoxy, each $Z^7$ can be methyl and each R can be —$CH_2CH_2$—, such that compound corresponding to Formula (III) can be 1,2-bis(methyldiethoxysilyl)ethane ($CH_3$ $(EtO)_2Si$—$CH_2CH_2$—$Si(EtO)_2CH_3$).

In a particular embodiment, each $Z^5$, $Z^6$ and $Z^7$ can be ethoxy and each R can be —$CH_2$—, such that compound corresponding to Formula (III) can be bis(triethoxysilyl)methane (($EtO)_3Si$—$CH_2$—$Si(EtO)_3$).

In a particular embodiment, each $Z^5$, $Z^6$ and $Z^7$ can be ethoxy and each R can be
—HC═CH—, such that compound corresponding to Formula (III) can be 1,2-bis(triethoxysilyl)ethylene (($EtO)_3Si$—HC═CH—$Si(EtO)_3$).

In a particular embodiment, each $Z^5$, $Z^6$ and $Z^7$ can be methoxy and each R can be

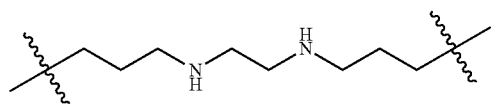

such that compound corresponding to Formula (III) can be N,N'-bis[(3-trimethoxysilyl)propyl]ethylenediamine.

In a particular embodiment, each $Z^5$ and $Z^6$ can be ethoxy, each $Z^7$ can be methyl and each R can be

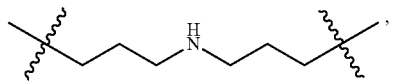 [SMILES: *CCCNCCC*]

such that compound corresponding to Formula (III) can be bis[(methyldiethoxysilyl)propyl]amine.

In a particular embodiment, each $Z^5$ and $Z^6$ can be methoxy, each $Z^7$ can be methyl and each R can be

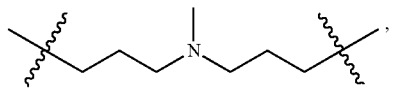 [SMILES: *CCCN(C)CCC*]

such that compound corresponding to Formula (III) can be bis[(methyldimethoxysilyl)propyl]-N-methylamine.

II.E. Trivalent Metal Oxide Sources

In additional embodiments, the methods provided herein can further comprise adding to the aqueous solution sources of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAlO_2$, boron nitride, $B_2O_3$ and/or $H_3BO_3$.

In various aspects, the source of trivalent metal oxide may be a compound of formula $M^1(OZ^8)_3$ (IV), wherein $M^1$ can be a Group 13 metal and each $Z^8$ independently can be a hydrogen atom, a $C_1$-$C_6$ alkyl group or a bond to a silicon atom of another compound.

In one embodiment, $M^1$ can be B, Al, Ga, In, Il, or Uut. In particular, $M^1$ can be Al or B.

Additionally or alternatively, each $Z^8$ can a hydrogen atom.

Additionally or alternatively, each $Z^8$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, each $Z^8$ can be methyl, ethyl, propyl or butyl.

Additionally or alternatively, each $Z^8$ can a bond to a silicon atom of another compound.

Additionally or alternatively, $M^1$ can be Al or B and each $Z^8$ can be, a hydrogen atom, methyl, ethyl, propyl butyl or a bond to a silicon atom of another compound.

Additionally or alternatively, $M^1$ can be Al or B and each $Z^8$ can be methyl, ethyl, propyl or butyl.

In a particular embodiment, $M^1$ can be Al and each $Z^8$ can be methyl, such that compound corresponding to Formula (IV) can be aluminum trimethoxide.

In a particular embodiment, $M^1$ can be Al and each $Z^8$ can be ethyl, such that compound corresponding to Formula (IV) can be aluminum triethoxide.

In a particular embodiment, $M^1$ can be Al and each $Z^8$ can be propyl, such that compound corresponding to Formula (IV) can be aluminum isopropoxide.

In a particular embodiment, $M^1$ can be Al and each $Z^8$ can be butyl, such that compound corresponding to Formula (IV) can be aluminum tri-sec-butoxide.

Additionally or alternatively, the source of trivalent metal oxide may be a compound of Formula $(Z^9O)_2M^2$-O-Si$(OZ^{10})_3$ (V), wherein $M^2$ can be a Group 13 metal and $Z^9$ and $Z^{10}$ each independently can be a hydrogen atom, a $C_1$-$C_6$ alkyl group or a bond to silicon atom of another compound.

In one embodiment, $M^2$ can be B, Al, Ga, In, Il, or Uut. In particular, $M^1$ can be Al or B.

Additionally or alternatively, $Z^9$ and $Z^{10}$ each independently can be a hydrogen atom.

Additionally or alternatively, $Z^9$ and $Z^{10}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^9$ and $Z^{10}$ each independently can be methyl, ethyl, propyl or butyl.

Additionally or alternatively, $Z^9$ and $Z^{10}$ each independently can be a bond to silicon atom of another compound.

Additionally or alternatively, $M^1$ can be Al or B and $Z^9$ and $Z^{10}$ each independently can be a hydrogen atom, methyl, ethyl, propyl, butyl or a bond to silicon atom of another compound.

Additionally or alternatively, $M^1$ can be Al or B and $Z^9$ and $Z^{10}$ each independently can be methyl, ethyl, propyl or butyl.

Additionally or alternatively, the source of a trivalent metal oxide may be a source of a compound of Formula (IV) (e.g., $AlCl_3$), and/or a source of a compound of Formula (V).

The molar ratio of compound of Formula (Ia) to compound of Formula (III) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (III) can be from about 4:1 to 1:4 or from about 2.5:1 to 1:2.5, about 2:1 to about 1:2, such as about 1.5:1 to about 1.5:1.

II.F. Compounds of Formula (VI)

In additional embodiments, the methods provided herein can further comprise adding at least one cyclic compound of Formula

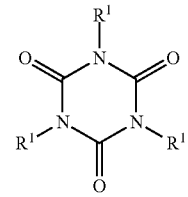

(VI)

into the aqueous mixture to form a solution, wherein each $R^1$ independently can be a $X^1OX^2X^3SiX^4$ group, wherein each $X^1$ can be a hydrogen atom, a $C_1$-$C_4$ alkyl group or a bond to a silicon atom of another compound; $X^2$ and $X^3$ each independently can be a hydroxyl group, a $C_1$-$C_4$ alkyl group, a $C_1$-$C_4$ alkoxy group or an oxygen atom bonded to a silicon atom of another compound; and each $X^4$ can be a $C_1$-$C_8$ alkylene group bonded to a nitrogen atom of the cyclic compound In various embodiments, each $X^1$ can be a hydrogen atom.

Additionally or alternatively, each $X^1$ can be a $C_1$-$C_4$ alkyl, a $C_1$-$C_3$ alkyl, a $C_1$-$C_2$ alkyl or methyl.

Additionally or alternatively, each $X^1$ can be a bond to a silicon atom of another compound.

Additionally or alternatively, each $X^2$ and $X^3$ each independently can be a hydroxyl group.

Additionally or alternatively, each $X^2$ and $X^3$ each independently can be a $C_1$-$C_4$ alkyl group, a $C_1$-$C_3$ alkyl group, a $C_1$-$C_2$ alkyl group or methyl.

Additionally or alternatively, each $X^2$ and $X^3$ each independently can be a $C_1$-$C_4$ alkoxy group, a $C_1$-$C_3$ alkoxy group, a $C_1$-$C_2$ alkoxy group or methoxy.

Additionally or alternatively, each $X^2$ and $X^3$ each independently can be a $C_1$-$C_2$ alkyl group or a $C_1$-$C_2$ alkoxy group.

Additionally or alternatively, each $X^2$ and $X^3$ each independently can be an oxygen atom bonded to a silicon atom of another compound.

Additionally or alternatively, each $X^1$ can be a hydrogen atom, a $C_1$-$C_2$ alkyl group or a bond to a silicon atom of another compound; and $X^2$ and $X^3$ each independently can be a hydroxyl group, a $C_1$-$C_2$ alkyl group, a $C_1$-$C_2$ alkoxy group or an oxygen atom bonded to a silicon atom of another compound.

Additionally or alternatively, each $X^1$ can be $C_1$-$C_2$ alkyl group; and $X^2$ and $X^3$ each independently can be a $C_1$-$C_2$ alkyl group or a $C_1$-$C_2$ alkoxy group.

Additionally or alternatively, each $X^4$ can be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound.

Additionally or alternatively, each $X^1$ can be a hydrogen atom, a $C_1$-$C_2$ alkyl group or a bond to a silicon atom of another compound; $X^2$ and $X^3$ each independently can be a hydroxyl group, a $C_1$-$C_2$ alkyl group, a $C_1$-$C_2$ alkoxy group or an oxygen atom bonded to a silicon atom of another compound; and $X^4$ can be a $C_1$-$C_4$ alkylene group bonded to a nitrogen atom of the cyclic compound.

Additionally or alternatively, each $X^1$ can be a $C_1$-$C_2$ alkyl group; $X^2$ and $X^3$ each independently can be a $C_1$-$C_2$ alkyl group or a $C_1$-$C_2$ alkoxy group; and $X^4$ can be a $C_1$-$C_4$ alkylene group bonded to a nitrogen atom of the cyclic compound.

In a particular embodiment, each $X^1$ can be methyl; $X^2$ and $X^3$ each independently can be methoxy; and $X^4$ can be —$CH_2CH_2CH_2$—, such that the compound corresponding to Formula (Ia) can be tris(3-trimethoxysilylpropyl)isocyanurate.

In some embodiments, only a compound of Formula (VI) (e.g., tris(3-trimethoxysilylpropyl)isocyanurate) may be added to the aqueous mixture and no other compounds of Formulas (I)-(V) are added. Additionally or alternatively, only a compound of Formula (VI) (e.g., tris(3-trimethoxysilylpropyl)isocyanurate) and a compound of Formula (II) (e.g., tetraethyl orthosilicate (TEOS) ((EtO)$_4$Si) may be added to the aqueous mixture and no other compounds of Formulas (I) and (III)-(V) are added.

II.G. Metal Chelate Sources

In additional embodiments, the methods provided herein can further comprise adding to the aqueous solution a source of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato)titanium, di-i-propoxy.bis(acetylacetonato)titanium, di-n-butoxy.bis(acetylacetonato)titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato) titanium, mono-i-propoxy.tris(acetylacetonato)titanium, mono-n-butoxy.tris(acetylacetonato)titanium, mono-sec-butoxy.tris(acetylacetonato)titanium, mono-t-butoxy-tris(acetylacetonato)titanium, tetrakis(acetylacetonato)titanium, triethoxy.mono(ethylacetoacetato)titanium, tri-n-propoxy.mono(ethylacetoacetato)titanium, tri-i-propoxy.mono(ethylacetoacetato) titanium, tri-n-butoxy.mono(ethylacetoacetato) titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoacetato)titanium, mono-i-propoxy.tris(ethylacetoacetato) titanium, mono-n-butoxy.tris(ethylacetoacetato)titanium, mono-sec-butoxy.tris(ethylacetoacetato)titanium, mono-t-butoxy.tris(ethylacetoacetato)titanium, tetrakis(ethylacetoacetato) titanium, mono(acetylacetonato)tris(ethylacetoacetato) titanium, bis(acetylacetonato)bis(ethylacetoacetato)titanium, and tris(acetylacetonato)mono(ethylacetoacetato)titanium; zirconium chelate compounds such as triethoxy.mono(acetylacetonato)zirconium, tri-n-propoxy.mono(acetylacetonato) zirconium, tri-i-propoxy.mono(acetylacetonato)zirconium, tri-n-butoxy.mono(acetylacetonato)zirconium, tri-sec-butoxy.mono(acetylacetonato)zirconium, tri-t-butoxy.mono(acetylacetonato)zirconium, diethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato) zirconium, mono-n-butoxy.tris(acetylacetonato)zirconium, mono-sec-butoxy.tris(acetylacetonato)zirconium, mono-t-butoxy.tris(acetylacetonato)zirconium, tetrakis(acetylacetonato) zirconium, triethoxy.mono(ethylacetoacetato)zirconium, tri-n-propoxy.mono(ethylacetoacetato)zirconium, tri-i-propoxy.mono(ethylacetoacetato) zirconium, tri-n-butoxy.mono(ethylacetoacetato)zirconium, tri-sec-butoxy.mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato) zirconium, di-sec-butoxy.bis(ethylacetoacetato)zirconium, di-t-butoxy.bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato) zirconium, mono-n-butoxy.tris(ethylacetoacetato)zirconium, mono-sec-butoxy.tris(ethylacetoacetato)zirconium, mono-t-butoxy.tris(ethylacetoacetato)zirconium, tetrakis(ethylacetoacetato) zirconium, mono(acetylacetonato)tris(ethylacetoacetato) zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato) aluminum. Of these, the chelate compounds of titanium or aluminum can be of note, of which the chelate compounds of titanium can be particularly of note. These metal chelate compounds may be used either singly or in combination II.H. Molar Ratio In the methods described herein, a molar ratio of Formula (Ia):Formula (Ia), Formula (Ia):Formula (II), Formula (Ia):Formula (III), Formula (III):Formula (II), Formula (Ia):Formula (IV), Formula (Ia):Formula (V); Formula (VI):(II) and Formula (Ia):Formula (VI) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used. For example, a molar ratio of Formula (Ia):Formula (Ia) can be about 3:2. A molar ratio of Formula (Ia):Formula (II) can be about 2:3, about 4:3, about 4:1 or about 3:2. A molar ratio of Formula (Ia):

Formula (III) can be about 2:3, and about 4:1. A molar ratio of Formula (III):Formula (II) can be about 5:2, about 1:1, about 1:2 or about 2:3. A molar ratio of Formula (Ia): Formula (IV) and Formula (Ia):Formula (V) can be about 15:1 or about 5:1. A molar ratio of Formula (Ia):Formula (VI) can be about 3:2. A molar ratio of Formula (VI): Formula (II) can be about 2:3.

For the sake of the following discussion, the compounds of Formula (Ia), (II) and (III) shall be referred to collectively as starting siloxane. Depending on the choice of starting materials, the solution may have a variety of compositions. For example, if base is used, the solution may have molar ratios of starting siloxane to $OH^-$ of from about 1:5 to about 1:20, such as from about 1:5 to about 1:15 or from about 1:5 to 1:10, or from about 1:6 to 1:20. If acid is used, the solution may have molar ratios of starting siloxane:$H^+$ of from about 50:1 to about 5:1, such as from about 45:1 to about 10:1. In both cases when acid or base is used, the molar ratios of starting siloxane to $H_2O$ may vary from about 1:50 to about 1:1000, such as from about 1:100 to about 1:500.

II.I. Adding Adsorbent Material to the Solution

In various aspects, the methods described herein comprise adding an adsorbent material to the solution to form a slurry. Optionally, the solution may be stirred for at least about 4 hours, at least about 6 hours, at least about 8 hours, at least about 12 hours, at least about 18 hours, or at least about 24 hours before the adsorbent material is added to the solution. The adsorbent material may be any suitable microporous material, mesoporous material, analogous periodic mesoporous material (e.g. MCM-41, MCM-48 and KIT-6,) metal oxide, carbon and combinations thereof. Examples of microporous materials include, but are not limited to, zeolites, titanosilicates, aluminophosphates (i.e., AlPO), MeAlPO (Me=Si, Ti, or Zr), silicoaluminophosphates (i.e., SAPO), metal-organic frameworks (MOFs) (e.g., zeolitic imidazolate frameworks (ZIFs)). Examples of ALPO Family members include, but are not limited to: ALPO-5, ALPO-11, ALPO-16, ALPO-18, ALPO-22, ALPO-34, ALPO-35, ALPO-47, ALPO-52, ALPO-61, ALPO-AFI, ALPO-kanemite, ALPO4-ZON, ALPO4-L, ALPO4-5, ALPO4-34, and meso-ALPO. Examples of SAPO family members include, but are not limited to: SAPO-5, SAPO-8, SAPO-11, SAPO-18, SAPO-23, SAPO-31, SAPO-34, SAPO-35, SAPO-37, SAPO-40, SAPO-44, SAPO-47, SAPO-SOD, SAPO4-L, meso-SAPO. Examples of MOF Family members include, but are not limited to: MOF-5, MOF-7, MIL-100, MIL101, ZIF-8, ZIF-11 etc. Examples of mesoporous materials include, but are not limited to M41S family materials (e.g., MCM-41, MCM-48, KIT-6). Examples of metal oxides include, but are not limited to silica (e.g., $SiO_2$), alumina (e.g., $Al_2O_3$), titanias (e.g., $TiO_2$, $Ti_2O_3$, TiO), magnesia (e.g., MgO), boria (e.g., $B_2O$, $B_2O3$, $B_6O$), clay, and combinations thereof. Examples of carbons include activated carbon, carbon molecular sieves, carbon nanotubes and combinations thereof.

In particular the adsorbent material is a zeolite. The zeolite may have a framework type selected from the following group of framework types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, THW, ISV, ITE, ITH, ITW, TWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Particular examples of these framework types can include BEA, CHA, CFI, CLO, DDR, DON, EMT, ERI, FER, FAU, LTL, LTA, MWW, MOZ, MFI, MFS, MEL, MEI, MTW, MOR, MTT, MAZ, MFS, MTN, NES and combinations and intergrowths thereof.

AEL, AFO, AHT, ATO, CAN, EUO, FER, HEU, IMF, ITH, LAU, MEL, MFI, MFS, MRE, MSE, MTT, MTW, MWW, NES, OBW, OSI, PON, RRO, SFF, SFG, STF, STI, SZR, TON, TUN and VET. A person of ordinary skill in the art knows how to make the aforementioned frameworks. For example, see the references provided in the International Zeolite Association's database of zeolite structures found at www.iza-structure.org/databases.

Generally, the zeolite employed in the present method as an adsorbent material can typically have a silica to alumina molar ratio of at least 2, e.g., from about 2 to about 500, or about 20 to about 200. In some cases, $SiO_2:Al_2O_3$ ratios can be from 2 to greater than 500, and essentially to pure $SiO_2$. Suitable zeolites can include, but are not necessarily limited to, ZSM-5, ZSM-11, ZSM-12, ZSM-23, ZSM-48, ZSM-57, ZSM-58 (DDR, Sigma 1, SSZ-28), MCM-22, MCM-49, NU-87, UTD-1, CIT-5, EMC-2, zeolite A (3A, 4A, 5A and intermediate sizes), zeolite Y, dealuminized Y, zeolite L (Linde Type L), mordenite, erionite, chabazite (including natural forms), zeolite beta, ITQ-29 ([Si]LTA), and the like, as well as intergrowths and combinations thereof. In certain embodiments, the zeolite can comprise, consist essentially of, or be ZSM-5.

Additionally or alternatively, the zeolite may be present at least partly in hydrogen form in the adsorbent material (e.g., HZSM-5). Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

Additionally or alternatively, the adsorbent material may be have a catalyst metal as described herein incorporated in the pores of the material.

II.J. Coating the Substrate

The methods described herein can further comprise coating the slurry onto a substrate. Optionally, the slurry may be agitated (e.g. via sonication) before coating on the substrate. Examples of substrates include, but are not limited to, a capillary tube, a microchannel, a monolith, a silica particle, which may be spherical, and a silicon wafer.

II. K. Aging the Slurry

The slurry formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days). In particular, the slurry can be aged for up to about 24 hours.

Additionally or alternatively, the solution formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the solution formed in the method can be aged at a temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C., at least about 125° C. at least about 130° C., at least about 140° C., at least about 150° C., at least about 175° C., at least about 200° C., at least about 250° C., or about 300° C.

Additionally or alternatively, the solution formed in the method can be aged at a temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 125° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 125° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 125° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70° C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 125° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 125° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 125° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C. In particular, the slurry is aged for the amount of time described above (e.g., up to about 24 hours, etc.) at a temperature of about 20° C. to about 125° C.

II.L. Drying the Slurry

The methods described herein comprise drying the slurry to obtain a coating comprising the adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

In some embodiments, the slurry formed in the method can be dried at a temperature of greater than or equal to about 25° C., greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the slurry formed in the method can be dried at temperature of about 25° C. to about 600° C., about 25° C. to about 550° C., about 25° C. to about 500° C., about 25° C. to about 450° C., about 25° C. to about 400° C., about 25° C. to about 350° C., about 25° C. to about 300° C., about 25° C. to about 250° C., about 25° C. to about 200° C., about 25° C. to about 150° C., about 25° C. to about 120° C., about 25° C. to about 110° C., about 25° C. to about 100° C., about 25° C. to about 80° C., about 25° C. to about 70° C., about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 80° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the slurry formed in the method can be dried at temperature from about 70° C. to about 150° C.

Additionally or alternatively, the slurry formed in the method can be dried in under a vacuum, in an inert atmosphere (e.g., $N_2$, Ar), a reducing atmosphere and/or air atmosphere.

More than one coating step may be performed to adjust the thickness of the coating on the substrate. Multiple coating steps may be performed to produce a thicker coating. In various aspects, the coating on the substrate may have thickness of up to about 0.10 μm, up to about 1.0 μm, up to about 10 μm, up to about 50 μm, up to about 100 μm, up to about 150 μm, up to about 200 μm, a up to about 250 μm, up to about 300 μm, up to about 350 μm, up to about 400 μm, up to about 450 μm, up to about 500 μm, up to about 550 μm, up to about 600 μm, up to about 650 μm, up to about 700 μm, up to about 750 μm, up to about 800 μm, up to about 850 μm, up to about 900 μm, up to about 950 μm, or up to about 1000 μm. In particular, the coating on the substrate may have thickness of up to about 150 μm.

Additionally or alternatively, the coating on the substrate may have thickness of about 0.10 μm to about 1000 μm, about 0.10 μm to about 950 μm, about 0.10 μm to about 900 μm, about 0.10 μm to about 850 μm, about 0.10 μm to about 800 μm, about 0.10 μm to about 750 μm, about 0.10 μm to about 700 μm, about 0.10 μm to about 650 μm, about 0.10 μm to about 600 μm, about 0.10 μm to about 550 μm, about 0.10 μm to about 500 μm, about 0.10 μm to about 450 μm, about 0.10 μm to about 400 μm, about 0.10 μm to about 350 μm, about 0.10 μm to about 300 μm, about 0.10 μm to about 250 μm, about 0.10 μm to about 200 μm, about 0.10 μm to about 250 μm, about 0.10 μm to about 200 μm, about 0.10 μm to about 150 μm, about 0.10 μm to about 100 μm, about 0.10 μm to about 50 μm, about 0.10 μm to about 10 μm, about 0.10 μm to about 1.0 μm, about 1.0 μm to about 1000 μm, about 1.0 μm to about 950 μm, about 1.0 μm to about 900 μm, about 1.0 μm to about 850 μm, about 1.0 μm to about 800 μm, about 1.0 μm to about 750 μm, about 1.0 μm to about 700 μm, about 1.0 μm to about 650 μm, about 1.0 μm to about 600 μm, about 1.0 μm to about 550 μm, about 1.0 μm to about 500 μm, about 1.0 μm to about 450 μm, about 1.0 μm to about 400 μm, about 1.0 μm to about 350 μm, about 1.0 μm to about 300 μm, about 1.0 μm to about 250 µm, about 1.0 µm to about 200 µm, about 1.0 µm to about 250 µm, about 1.0 µm to about 200 µm, about 1.0 µm to about 150 µm, about 1.0 µm to about 100 µm, about 1.0 µm to about 50 µm or about 1.0 µm to about 10 µm. In particular, the coating on the substrate may have thickness of about 0.10 µm to about 1000 µm, about 0.10 µm to about 500 µm, about 1.0 µm to about 500 µm or about 1.0 µm to about 150 µm.

In some cases, when the substrate is a capillary tube, the coating on the capillary tube may be up to about 10%, up to about 20%, up to about 30% or up to about 40% of the inner diameter of the capillary tube.

II.M. Optional Further Steps

In some embodiments, the method can further comprise calcining the organosilica material and/or coating to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 500° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 500° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

Additionally or alternatively, the method as described herein may not include a calcining step.

In some embodiments, the method can further comprise incorporating a catalyst metal within the pores of the organosilica material and/or the adsorbent material. Exemplary catalyst metals can include, but are not limited to, a Group 6 element, a Group 8 element, a Group 9 element, a Group 10 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum.

The catalyst metal can be incorporated into the organosilica material and/or adsorbent material by any convenient method, such as by impregnation, by ion exchange, or by complexation to surface sites. The catalyst metal so incorporated may be employed to promote any one of a number of catalytic transformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be silica-alumina, alumina and/or a zeolite, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material ranging from about 80 parts support material to 20 parts binder material to 20 parts support material to 80 parts binder material, all ratios being by weight, typically from 80:20 to 50:50 support material: binder material, prefer ably from 65:35 to 35:65. Compositing may be done by conventional means including mulling the materials together followed by extrusion of pelletizing into the desired finished catalyst particles.

In some embodiments, the method can further comprise incorporating cationic metal sites into the network structure of the organosilica material and/or the adsorbent material by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the method can further comprise incorporating a surface metal within the pores of the organosilica material and/or the adsorbent material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material and/or adsorbent material. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material and/or the adsorbent material. The surface metal(s) can be incorporated into/onto the organosilica material and/or the adsorbent material by any convenient method, such as by impregnation, deposition, grafting, co-condensation, by ion exchange, and/or the like.

In some embodiments, the substrate may be pre-treated prior to coating. In various aspects, pre-treating the substrate may comprise applying a solution comprising an oxidizing agent and optionally an inorganic acid as described herein. Examples of suitable oxidizing agents include, but are not limited to, hydrogen peroxide and sulfuric acid. For example, one may use hydrogen peroxide only or both hydrogen peroxide and sulfuric acid to pre-treat the substrate prior to coating.

Additionally or alternatively, an alcohol may be added to the solution described herein. As used herein, the term "alcohol" refers to a hydroxy group (—OH) bound to a saturated carbon atom (i.e., an alkyl). Examples of the alkyl portion of the alcohol include, but are not limited to propyl, butyl, pentyl, hexyl, iso-propyl, iso-butyl, sec-butyl, tert-butyl, etc. The alcohol may be straight or branched. "Alcohol" is intended to embrace all structural isomeric forms of an alcohol. Examples of suitable alcohols include, but are not limited to, $C_1$-$C_6$ alcohols or $C_1$-$C_4$ alcohols, such as methanol, ethanol, propanol, isopropanol, butanol, isobutanol, n-butanol, tert-butanol, pentanol and hexanol. Particularly, the alcohol may be ethanol.

Additionally or alternatively, the methods described herein can further comprise adding an additional amount of any one of compounds of Formulas (Ia) and (II)-(VI) to the slurry. In particular, an additional amount of a compound of Formula (Ia) (e.g. 1,1,3,3,5,5-hexaethoxy-1,3,5-trisilacyclohexane) may be added to the slurry.

Additionally or alternatively, the methods described herein can further comprise supplying a purge gas to the substrate after coating. The purge gas may be any suitable inert gas (e.g. $N_2$, Ar, etc.).

III. ORGANOSILICA MATERIAL-COATED SUBSTRATES

Organosilica material-coated substrates can be made by the methods described herein.

In some cases, the organosilica material-coated substrate may be used in chromatography, e.g., gas chromatography, liquid chromatography and/or supercritical chromatography.

In various aspects, the coating on the substrate may comprise the organosilica material as a binder in an amount of about 1%, about 5%, about 10%, about 15%, about 20%, about 25%, about 30%, about 35%, about 40%, about 45%, about 50%, about 55%, about 60%, about 65%, about 70%, or about 75%. In particular, the coating on the substrate may comprise the organosilica material as a binder in an amount of about 1% to about 75%, about 1% to about 60%, about 1% to about 50% or about 10% to about 50%.

As described above, the coating comprises the adsorbent material as a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

In one embodiment, each $Z^3$ can be a hydroxyl group.

Additionally or alternatively, each $Z^3$ can be a $C_1$-$C_4$ alkoxy group, a $C_1$-$C_3$ alkoxy group, a $C_1$-$C_2$ alkoxy group, or methoxy.

Additionally or alternatively, each $Z^3$ can be an oxygen atom bonded to a silicon atom of another unit or an active site on the substrate.

Additionally or alternatively, each $Z^3$ can be a hydroxyl group, a $C_1$-$C_2$ alkoxy group, or an oxygen atom bonded to a silicon atom of another unit or an active site on the substrate.

Additionally or alternatively, each $Z^4$ can be a hydroxyl group.

Additionally or alternatively, each $Z^4$ can be a $C_1$-$C_4$ alkoxy group, a $C_1$-$C_3$ alkoxy group, a $C_1$-$C_2$ alkoxy group, or methoxy.

Additionally or alternatively, each $Z^4$ can be a $C_1$-$C_4$ alkyl group, a $C_1$-$C_3$ alkyl group, a $C_1$-$C_2$ alkyl group, or methyl.

Additionally or alternatively, each $Z^4$ can be an oxygen atom bonded to a silicon atom of another unit or an active site on the substrate.

Additionally or alternatively, each $Z^4$ can be a hydroxyl group, a $C_1$-$C_2$ alkoxy group, a $C_1$-$C_2$ alkyl group, or an oxygen atom bonded to a silicon atom of another unit or an active site on the substrate.

Additionally or alternatively, each $Z^3$ can be a hydroxyl group, a $C_1$-$C_2$ alkoxy group, or an oxygen atom bonded to a silicon atom of another unit or an active site on the substrate and each $Z^4$ can be a hydroxyl group, a $C_1$-$C_2$ alkyl group, a $C_1$-$C_2$ alkoxy group, or an oxygen atom bonded to a silicon atom of another unit or an active site on the substrate.

Additionally or alternatively, each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate.

Additionally or alternatively, each $Z^3$ can be a hydroxyl group or an oxygen atom bonded to a silicon atom of another unit or an active site on the substrate and each $Z^4$ can be a hydroxyl group, or an oxygen atom bonded to a silicon atom of another unit or an active site on the substrate.

If a compound of Formula (Ia) is used in the methods described herein, the organosilica material made can be a homopolymer comprising independent units of Formula I.

In a particular embodiment, if a compound of Formula (Ia), such as $[(EtO)_2SiCH_2]_3$, is used in the methods described herein, the organosilica material made can be a homopolymer comprising independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate.

In another particular embodiment, if two compounds of Formula (Ia), such as $[(EtO)_2SiCH_2]_3$ and $[EtOCH_3SiCH_2]_3$, are used in the methods described herein, the organosilica material made can be a copolymer comprising: independent units of Formula I, wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (I), wherein each $Z^3$ can be a hydroxyl group, ethoxy, or an oxygen atom bonded to a silicon atom of another unit or an active site on the substrate and each $Z^4$ can be methyl.

If a compound of Formula (Ia) and a compound of Formula (II) are used in the methods described herein, the organosilica material made can be a copolymer comprising independent units of Formula I and independent units of Formula $Z^{11}OZ^{12}Z^{13}Z^{14}$ (VI), wherein each $Z^{11}$ can be a hydrogen atom or a $C_1$-$C_4$ alkyl group or a bond to a silicon atom of another monomer or an active site on the substrate; and $Z^{12}$, $Z^{13}$ and $Z^{14}$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer or an active site on the substrate.

In another particular embodiment, if a compound of Formula (Ia), such as $[(EtO)_2SiCH_2]_3$, and a compound of Formula (II), such as tetraethyl orthosilicate (TEOS), are used in the methods described herein, the organosilica material made can be a copolymer comprising: independent units of Formula (I), wherein each $Z^3$ can be a hydroxyl group, ethoxy, or an oxygen atom bonded to a silicon atom of another monomer or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer or an active site on the substrate; and $Z^{12}$, $Z^{13}$ and $Z^{14}$ each independently can be selected from the group consisting of a hydroxyl group, ethoxy, and an oxygen atom bonded to a silicon atom of another monomer or an active site on the substrate.

In another particular embodiment, if a compound of Formula (Ia), such as $[(EtO)_2SiCH_2]_3$, and compound of Formula (II), such as methyltriethoxysilane (MTES), are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be methyl.

In another particular embodiment, if a compound of Formula (Ia), such as $[(EtO)_2SiCH_2]_3$, and compound of Formula (II), such as (N,N-dimethylaminopropyl) trimethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, methyl or a bond to a silicon atom of another monomer or an active site on the substrate; $Z^{12}$, $Z^{13}$ each independently can be selected from the group consisting of a hydroxyl group, methoxy, and an oxygen atom bonded to a silicon atom of another monomer or an active site on the substrate; and $Z^{14}$ can be

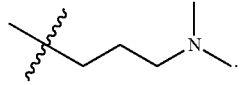 [SMILES: *CCCN(C)C]

In another particular embodiment, if a compound of Formula (Ia), such as $[(EtO)_2SiCH_2]_3$, and compound of Formula (II), such as (N-(2-aminoethyl)-3-aminopropyltriethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer or an active site on the substrate; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be

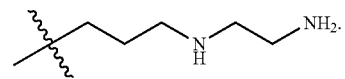 [SMILES: *CCCNCCN]

In another particular embodiment, if a compound of Formula (Ia), such as $[(EtO)_2SiCH_2]_3$, and compound of Formula (II), such as 4-methyl-1-(3-triethoxysilylpropyl)-piperazine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be

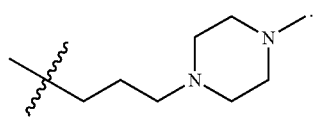 [SMILES: *CCCN1CCN(C)CC1]

In another particular embodiment, if a compound of Formula (Ia), such as $[(EtO)_2SiCH_2]_3$, and compound of Formula (II), such as 4-(2-(triethoxysilyl)ethyl)pyridine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be

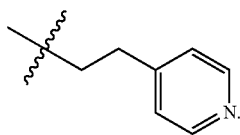 [SMILES: *CCc1ccncc1]

In another particular embodiment, if a compound of Formula (Ia), such as $[(EtO)_2SiCH_2]_3$, and compound of Formula (II), such as 1-(3-(triethoxysilyl)propyl)-4,5-dihydro-1H-imidazole, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be

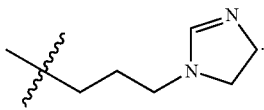 [SMILES: *CCCN1C=NCC1]

In another particular embodiment, if a compound of Formula (Ia), such as $[(EtO)_2SiCH_2]_3$, and compound of Formula (II), such as (3-aminopropyl)triethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the substrate; and each $Z^{14}$ can be

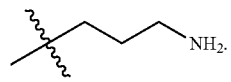

If a compound of Formula (Ia) and a compound of Formula (III) are used in the methods described herein, the organosilica material made can be a copolymer comprising independent units of Formula I and independent units of Formula $Z^{15}Z^{16}Z^{17}Si—R^5—SiZ^{15}Z^{16}Z^{17}$ (VII), wherein each $Z^{15}$ independently can be a hydroxyl group, a $C_1$-$C_4$ alkoxy group or an oxygen atom bonded to a silicon atom of another monomer or an active site on the substrate; $Z^{16}$ and $Z^{17}$ each independently can be a hydroxyl group, a $C_1$-$C_4$ alkoxy group, a $C_1$-$C_4$ alkyl group or an oxygen atom bonded to a silicon atom of another monomer or an active site on the substrate; and each $R^5$ can be selected from the group consisting of a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

In another particular embodiment, if a compound of Formula (Ia), such as $[(EtO)_2SiCH_2]_3$, and compound of Formula (III), such as (1,2-bis(methyldiethoxysilyl)ethane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, an ethoxy or an oxygen atom bonded to a silicon atom of another monomer or an active site on the substrate; each $Z^{16}$ can be a hydroxyl group, an ethoxy group or an oxygen atom bonded to a silicon atom of another monomer or an active site on the substrate; each $Z^{17}$ can be methyl; and each $R^5$ can be —$CH_2CH_2$—.

In another particular embodiment, if a compound of Formula (Ia), such as $[(EtO)_2SiCH_2]_3$, and compound of Formula (III), such as (bis(triethoxysilyl)methane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, an ethoxy or an oxygen atom bonded to a silicon atom of another monomer or an active site on the substrate; $Z^{16}$ and $Z^{17}$ can be each independently selected from the group consisting of a hydroxyl group, an ethoxy group or an oxygen atom bonded to a silicon atom of another monomer or an active site on the substrate; and each $R^5$ can be —$CH_2$—.

In another particular embodiment, if a compound of Formula (Ia), such as $[(EtO)_2SiCH_2]_3$, and compound of Formula (III), such as 1,2-bis(triethoxysilyl)ethylene, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, an ethoxy or an oxygen atom bonded to a silicon atom of another monomer or an active site on the substrate; $Z^{16}$ and $Z^{17}$ can be each independently selected from the group consisting of a hydroxyl group, an ethoxy group or an oxygen atom bonded to a silicon atom of another monomer or an active site on the substrate; and each $R^5$ can be —HC═CH—.

In another particular embodiment, if a compound of Formula (Ia), such as $[(EtO)_2SiCH_2]_3$, and compound of Formula (III), such as N,N'-bis[(3-trimethoxysilyl)propyl]ethylenediamine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, an methoxy or an oxygen atom bonded to a silicon atom of another monomer or an active site on the substrate; each $Z^{16}$ and $Z^{17}$ can be each independently selected from the group consisting of a hydroxyl group, an methoxy group or an oxygen atom bonded to a silicon atom of another monomer or an active site on the substrate; and each $R^5$ can be

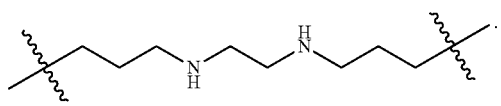 [SMILES: *CCCNCCNCCC*]

In another particular embodiment, if a compound of Formula (Ia), such as $[(EtO)_2SiCH_2]_3$, and compound of Formula (III), such as bis[(methyldiethoxysilyl)propyl]amine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, an ethoxy or an oxygen atom bonded to a silicon atom of another monomer or an active site on the substrate; each $Z^{16}$ can be a hydroxyl group, an ethoxy group or an oxygen atom bonded to a silicon atom of another monomer or an active site on the substrate; $Z^{17}$ can be methyl; and each $R^5$ can be

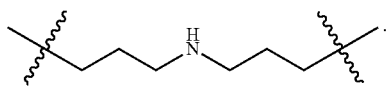

In another particular embodiment, if a compound of Formula (Ia), such as $[(EtO)_2SiCH_2]_3$, and compound of Formula (III), such as bis[(methyldimethoxysilyl)propyl]-N-methylamine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (VII), wherein each $Z^{15}$ can be a hydroxyl group, a methoxy or an oxygen atom bonded to a silicon atom of another monomer or an active site on the substrate; each $Z^{16}$ can be a hydroxyl group, a methoxy group or an oxygen atom bonded to a silicon atom of another monomer or an active site on the substrate; $Z^{17}$ can be methyl; and each $R^5$ can be

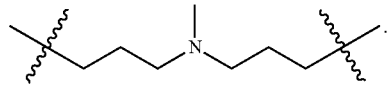 [SMILES: *CCCN(C)CCC*]

If a compound of Formula (Ia) and a compound of Formula (IV) are used in the methods described herein, the organosilica material made can be a copolymer comprising independent units of Formula I and independent units of Formula $M^3(OZ^{18})_3$ (VIII), wherein $M^3$ can be a Group 13 metal and each $Z^{18}$ independently can be a hydrogen atom, a $C_1$-$C_6$ alkyl or a bond to a silicon atom of another monomer or an active site on the substrate.

In another particular embodiment, if a compound of Formula (Ia), such as $[(EtO)_2SiCH_2]_3$, and compound of Formula (IV), such as aluminum tri-sec-butoxide, are used in the methods described herein, the organosilica material made can be a copolymer comprising: independent units of Formula (I), wherein $Z^3$ can be a hydroxyl group, ethoxy, or an oxygen atom bonded to a silicon atom of another unit or an active site on the substrate and $Z^4$ can be a hydroxyl group, ethoxy, or an oxygen atom bonded to a silicon atom of another unit or an active site on the substrate; and independent units of Formula (VIII), wherein $M^{13}$ can be a Group 13 metal and $Z^{18}$ can be a hydrogen atom, a sec-butyl or a bond to a silicon atom of another monomer or an active site on the substrate.

If a compound of Formula (Ia) and a compound of Formula (V) are used in the methods described herein, the organosilica material made can be a copolymer comprising independent units of Formula I and independent units of Formula $(Z^{19}O)_2M^4$-O—$Si(OZ^{20})_3$ (IX), wherein $M^4$ represents a Group 13 metal and $Z^{19}$ and $Z^{20}$ each independently represent a hydrogen atom, a $C_1$-$C_6$ alkyl group or a bond to a silicon atom of another monomer or an active site on the substrate.

If a compound of Formula (Ia) and a compound of Formula (VI) are used in the methods described herein, the organosilica material made can be a copolymer comprising independent units of Formula I and independent cyclic polyurea units of Formula

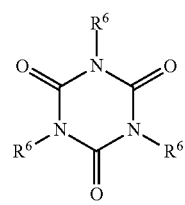

(X)

wherein each $R^6$ independently can be a $Z^{21}OZ^{22}Z^{23}SiZ^{24}$ group, wherein each $Z^{21}$ can be a hydrogen atom, a $C_1$-$C_4$ alkyl group, or a bond to a silicon atom of another monomer unit or an active site on the substrate; $Z^{22}$ and $Z^{23}$ each independently can be a hydroxyl group, a $C_1$-$C_4$ alkyl group, a $C_1$-$C_4$ alkoxy group or an oxygen atom bonded to a silicon atom of another monomer unit or an active site on the substrate; and each $Z^{24}$ can be a $C_1$-$C_8$ alkylene group bonded to a nitrogen atom of the cyclic polyurea.

In another particular embodiment, if only a compound of Formula (VI), such as tris(3-trimethoxysilylpropyl)isocyanurate is used in the methods described herein, the organosilica material made can be a homopolymer comprising: independent units of Formula (X), wherein each $Z^{21}$ can be a hydrogen atom, methyl, or a bond to a silicon atom of another monomer or an active site on the substrate; $Z^{22}$ and $Z^{23}$ each independently can be a hydroxyl group, methoxy or an oxygen atom bonded to a silicon atom of another monomer unit or an active site on the substrate; and $Z^{24}$ can be —CH$_2$CH$_2$CH$_2$— bonded to a nitrogen atom of the cyclic polyurea.

In another particular embodiment, if a compound of Formula (Ia), such as [(EtO)$_2$SiCH$_2$]$_3$, and compound of Formula (VI), such as tris(3-trimethoxysilylpropyl)isocyanurate, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the substrate and each $Z^4$ can be a hydroxyl group, ethoxy, or an oxygen atom bonded to a silicon atom of another unit or an active site on the substrate; and independent units of Formula (X), wherein each $Z^{21}$ can be a hydrogen atom, methyl, or a bond to a silicon atom of another monomer or an active site on the substrate; $Z^{22}$ and $Z^{23}$ each independently can be a hydroxyl group, methoxy or an oxygen atom bonded to a silicon atom of another monomer unit or an active site on the substrate; and $Z^{24}$ can be —CH$_2$CH$_2$CH$_2$— bonded to a nitrogen atom of the cyclic polyurea.

In another particular embodiment, if a compound of compound of Formula (II), such as tetraethyl orthosilicate (TEOS) and compound of Formula (VI), such as tris(3-trimethoxysilylpropyl)isocyanurate, are used in the methods described herein, the organosilica material made can be a copolymer comprising: independent units of Formula (VI), wherein each $Z^{11}$ can be a hydrogen atom, ethyl or a bond to a silicon atom of another monomer or an active site on the substrate; and $Z^{12}$, $Z^{13}$ and $Z^{14}$ each independently can be selected from the group consisting of a hydroxyl group, ethoxy, and an oxygen atom bonded to a silicon atom of another monomer or an active site on the substrate; and independent units of Formula (X), wherein each $Z^{21}$ can be a hydrogen atom, methyl, or a bond to a silicon atom of another monomer or an active site on the substrate; $Z^{22}$ and $Z^{23}$ each independently can be a hydroxyl group, methoxy or an oxygen atom bonded to a silicon atom of another monomer unit or an active site on the substrate; and $Z^{24}$ can be —CH$_2$CH$_2$CH$_2$— bonded to a nitrogen atom of the cyclic polyurea.

The organosilica materials made by the methods described herein can be characterized as described in the following sections.

III. A. X-Ray Diffraction Peaks

The organosilica materials made by the methods described herein and used as a binder can exhibit powder X-ray diffraction patterns with one broad peak between about 1 and about 4 degrees 2θ, particularly one broad peak between about 1 and about 3 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

III.B. Silanol Content

In various aspects, the organosilica material used as a binder herein can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica material used as a binder herein may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

III.C. Pore Size

The organosilica material produced by the methods described herein and used as a binder can advantageously be in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material used as a binder can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica material used as a binder can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica material used as a binder can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica material can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm.

In one particular embodiment, the organo silica material produced by the methods described herein can have an average pore diameter of about 1.0 nm to about 30.0 nm, particularly about 1.0 nm to about 25.0 nm, particularly about 1.5 nm to about 25.0 nm, particularly about 2.0 nm to about 25.0 nm, particularly about 2.0 nm to about 20.0 nm, particularly about 2.0 nm to about 15.0 nm, or particularly about 2.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from $N_2$ adsorption isotherm experiments. In such circumstances, without being bound by theory, the hysteresis can result from the lack of regularity in the pore shapes/sizes and/or from bottleneck constrictions in such irregular pores.

III.D. Surface Area

The surface area of the organosilica material can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica material can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 m²/g, greater than or equal to about 550 m²/g, greater than or equal to about 600 m²/g, greater than or equal to about 700 m²/g, greater than or equal to about 800 m²/g, greater than or equal to about 850 m²/g, greater than or equal to about 900 m²/g, greater than or equal to about 1,000 m²/g, greater than or equal to about 1,050 m²/g, greater than or equal to about 1,100 m²/g, greater than or equal to about 1,150 m²/g, greater than or equal to about 1,200 m²/g, greater than or equal to about 1,250 m²/g, greater than or equal to about 1,300 m²/g, greater than or equal to about 1,400 m²/g, greater than or equal to about 1,450 m²/g, greater than or equal to about 1,500 m²/g, greater than or equal to about 1,550 m²/g, greater than or equal to about 1,600 m²/g, greater than or equal to about 1,700 m²/g, greater than or equal to about 1,800 m²/g, greater than or equal to about 1,900 m²/g, greater than or equal to about 2,000 m²/g, greater than or equal to greater than or equal to about 2,100 m²/g, greater than or equal to about 2,200 m²/g, greater than or equal to about 2,300 m²/g or about 2,500 m²/g.

Additionally or alternatively, the organosilica material may have a total surface area of about 50 m²/g to about 2,500 m²/g, about 50 m²/g to about 2,000 m²/g, about 50 m²/g to about 1,500 m²/g, about 50 m²/g to about 1,000 m²/g, about 100 m²/g to about 2,500 m²/g, about 100 m²/g to about 2,300 m²/g, about 100 m²/g to about 2,200 m²/g, about 100 m²/g to about 2,100 m²/g, about 100 m²/g to about 2,000 m²/g, about 100 m²/g to about 1,900 m²/g, about 100 m²/g to about 1,800 m²/g, about 100 m²/g to about 1,700 m²/g, about 100 m²/g to about 1,600 m²/g, about 100 m²/g to about 1,550 m²/g, about 100 m²/g to about 1,500 m²/g, about 100 m²/g to about 1,450 m²/g, about 100 m²/g to about 1,400 m²/g, about 100 m²/g to about 1,300 m²/g, about 100 m²/g to about 1,250 m²/g, about 100 m²/g to about 1,200 m²/g, about 100 m²/g to about 1,150 m²/g, about 100 m²/g to about 1,100 m²/g, about 100 m²/g to about 1,050 m²/g, about 100 m²/g to about 1,000 m²/g, about 100 m²/g to about 900 m²/g, about 100 m²/g to about 850 m²/g, about 100 m²/g to about 800 m²/g, about 100 m²/g to about 700 m²/g, about 100 m²/g to about 600 m²/g, about 100 m²/g to about 550 m²/g, about 100 m²/g to about 500 m²/g, about 100 m²/g to about 450 m²/g, about 100 m²/g to about 400 m²/g, about 100 m²/g to about 300 m²/g, about 100 m²/g to about 200 m²/g, about 200 m²/g to about 2,500 m²/g, about 200 m²/g to about 2,300 m²/g, about 200 m²/g to about 2,200 m²/g, about 200 m²/g to about 2,100 m²/g, about 200 m²/g to about 2,000 m²/g, about 200 m²/g to about 1,900 m²/g, about 200 m²/g to about 1,800 m²/g, about 200 m²/g to about 1,700 m²/g, about 200 m²/g to about 1,600 m²/g, about 200 m²/g to about 1,550 m²/g, about 200 m²/g to about 1,500 m²/g, about 200 m²/g to about 1,450 m²/g, about 200 m²/g to about 1,400 m²/g, about 200 m²/g to about 1, 300 m²/g, about 200 m²/g to about 1,250 m²/g, about 200 m²/g to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about 1,300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1, 300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organosilica material described herein may have a total surface area of about 100 m²/g to about 2,500 m² g, particularly about 200 m²/g to about 2,500 m²/g, particularly about 200 m²/g to about 2,000 m²/g, particularly about 500 m²/g to about 2,000 m²/g, or particularly about 1,000 m²/g to about 2,000 m²/g.

III.E. Pore Volume

The pore volume of the organosilica material made by the methods described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica material can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

IV. USES OF THE ORGANOSILICA MATERIAL-COATED SUBSTRATES

The organosilica materials obtainable by the method of the present invention find uses in several areas.

In certain embodiments, the organosilica material described herein can be used as adsorbents for gas and liquid separation.

IV.A. Chromatography

In some cases, the organosilica material-coated substrate may be used in chromatography, e.g., gas chromatography, liquid chromatography and/or supercritical chromatography. The organosilica material-coated substrate can be present in a chromatography column and contacted with an analyte in a gas, liquid and/or supercritical chromatography process.

In another embodiment, a method of preparing a chromatography column is provided. The method comprises: (a) adding at least one compound of Formula $[Z^1Z^2SiCH_2]_3$ (Ia) as described herein, and optionally at least one compound of Formulas (II)-(VI) as described herein into an aqueous mixture that contains essentially no structure directing agent or porogen to form a solution; (c) coating the slurry as described herein onto a chromatography column; (d) aging the slurry as described herein; and (e) drying the slurry as described herein to obtain a coating comprising the adsorbent material as described herein and a binder comprising an organosilica material as described herein.

IV.B. Gas Separation Processes

In some cases, the organosilica material-coated substrate can be used in a gas separation process as provided herein. The gas separation process can comprise contacting a gas mixture containing at least one contaminant with the organosilica material-coated substrate described herein as prepared according to the methods described herein.

In various embodiments, the gas separation process can be achieved by swing adsorption processes, such as pressure swing adsorption (PSA) and temperature swing adsorption (TSA). All swing adsorption processes typically have an adsorption step in which a feed mixture (typically in the gas phase) is flowed over an adsorbent to preferentially adsorb a more readily adsorbed component relative to a less readily adsorbed component. A component may be more readily adsorbed because of kinetic or equilibrium properties of the adsorbent. The adsorbent or organosilica material-coated substrate can typically be contained in a contactor that is part of the swing adsorption unit. The contactor can typically contain an engineered structured adsorbent bed or a particulate adsorbent bed. The bed can contain the organosilica material-coated substrate and other materials such as other adsorbents, mesopore filling materials, and/or inert materials used to mitigated temperature excursions from the heat of adsorption and desorption. Other components in the swing adsorption unit can include, but are not necessarily limited to, valves, piping, tanks, and other contactors. Swing adsorption processes are described in detail in U.S. Pat. Nos. 8,784,533; 8,784,534; 8,858,683; and 8,784,535, each of which are incorporated herein by reference. Examples of processes that can be used herein either separately or in combination are PSA, TSA, pressure temperature swing adsorption (PTSA), partial purge displacement swing adsorption (PPSA), PPTSA, rapid cycle PSA (RCPSA), RCTSA, RCPPSA and RCPTSA.

PSA processes rely on the fact that gases under pressure tend to be adsorbed within the pore structure of the adsorbent materials (e.g., the organosilica material described herein). Typically, the higher the pressure, the greater the amount of targeted gas component that will be adsorbed. When the pressure is reduced, the adsorbed targeted component is typically released, or desorbed. PSA processes can be used to separate gases of a gas mixture, because different gases tend to fill the pores or free volume of the adsorbent to different extents due to either the equilibrium or kinetic properties of the adsorbent. In many important applications, to be described as "equilibrium-controlled" processes, the adsorptive selectivity is primarily based upon differential equilibrium uptake of the first and second components. In another important class of applications, to be described as "kinetic-controlled" processes, the adsorptive selectivity is primarily based upon the differential rates of uptake of the first and second components.

If a gas mixture, such as natural gas, is passed under pressure through a vessel containing a polymeric or microporous adsorbent that is more selective towards carbon dioxide than it is for methane, at least a portion of the carbon dioxide can be selectively adsorbed by the adsorbent, and the gas exiting the vessel can be enriched in methane. When the adsorbent (e.g., the organosilica material described herein) reaches the end of its capacity to adsorb carbon dioxide, it can be regenerated by reducing the pressure, thereby releasing the adsorbed carbon dioxide. The adsorbent can then typically purged and repressurized and ready for another adsorption cycle.

TSA processes also rely on the fact that gases under pressure tend to be adsorbed within the pore structure of the adsorbent materials. When the temperature of the adsorbent (e.g., the organosilica material described herein) is increased, the adsorbed gas is typically released, or desorbed. By cyclically swinging the temperature of adsorbent beds, TSA processes can be used to separate gases in a mixture when used with an adsorbent selective for one or more of the components in a gas mixture. Partial pressure purge displacement (PPSA) swing adsorption processes regenerate the adsorbent with a purge. Rapid cycle (RC) swing adsorption processes complete the adsorption step of a swing adsorption process in a short amount of time. For kinetically selective adsorbents, it can be preferable to use a rapid cycle swing adsorption process. If the cycle time becomes too long, the kinetic selectivity can be lost. These swing adsorption protocols can be performed separately or in combinations. Examples of processes that can be used herein either separately or in combination are PSA, TSA, pressure temperature swing adsorption (PTSA), partial purge displacement swing adsorption (PPSA), PPTSA, rapid cycle PSA (RCPSA), RCTSA, vacuum pressure swing adsorption (VPSA), RCPPSA and RCPTSA.

In PSA processes, a feed gas mixture containing the first and second gas components is separated by cyclic variations of pressure coordinated with cyclic reversals of flow direction in a flow path contacting a fixed bed of the adsorbent material in an adsorber vessel. In the case of TSA or PPSA processes, cyclic variations of temperature and/or partial pressure of the gas components may be coordinated with gas flow through a flow path to perform a separation. The process in any specific PSA application operates at a cyclic frequency characterized by its period, and over a pressure envelope between a first relatively higher pressure and a second relatively lower pressure. Separation in PSA is achieved by coordinating the pressure variations with the flow pattern within the flow path, so that the gas mixture in the flow path is enriched in the second component (owing to preferential adsorptive uptake of the first component in the adsorbent material) when flowing in a first direction in the flow path, while the gas mixture is enriched in the first component (which has been desorbed by the adsorbent material) when flowing in the opposite direction in the flow path. In order to achieve separation performance objectives (i.e. product gas purity, recovery and productivity), process parameters and operating conditions should be designed to achieve a sufficiently high adsorptive selectivity of the first and second components over the adsorbent material, at the cyclic frequency and within the pressure envelope.

Swing adsorption processes can be applied to remove a variety of target gases, also referred to as "contaminant gas" from a wide variety of gas mixtures. Typically, in binary separation systems, the "light component" as utilized herein is taken to be the species or molecular component(s) not preferentially taken up by the adsorbent in the adsorption step of the process. Conversely in such binary systems, the "heavy component" as utilized herein is typically taken to be the species or molecular component(s) preferentially taken up by the adsorbent in the adsorption step of the process. However, in binary separation systems where the Component(s) that is(are) preferentially adsorbed has(have) a lower molecular weight than the component(s) that is(are) not preferentially adsorbed, those descriptions may not necessarily correlate as disclosed above.

An example of gas mixture that can be separated in the methods described herein is a gas mixture comprising $CH_4$, such as a natural gas stream. A gas mixture comprising $CH_4$ can contain significant levels of contaminants such as $H_2O$, $H_2S$, $CO_2$, $N_2$, mercaptans, and/or heavy hydrocarbons. Additionally or alternatively, the gas mixture can comprise $NO_x$ and/or $SO_x$ species as contaminants, such as a waste gas stream, a flue gas stream and a wet gas stream. As used herein, the terms "$NO_x$," and "$NO_x$" species refers to the various oxides of nitrogen that may be present in waste gas, such as waste gas from combustion processes. The terms refer to all of the various oxides of nitrogen including, but not limited to, nitric oxide (NO), nitrogen dioxide ($NO_2$), nitrogen peroxide ($N_2O$), nitrogen pentoxide ($N_2O_5$), and mixtures thereof. As used herein, the terms "$SO_x$," and "$SO_x$ species," refers to the various oxides of sulfur that may be present in waste gas, such as waste gas from combustion processes. The terms refer to all of the various oxides of sulfur including, but not limited to, SO, $SO_2$, $SO_3$, $SO_4$, $SO_2$ and $S_6O_2$. Thus, examples of contaminants include, but are not limited to $H_2O$, $H_2S$, $CO_2$, $N_2$, mercaptans, heavy hydrocarbons, $NO_x$ and/or $SO_x$ species. In particular, the gas mixture may comprise $CH_4$ and the at least one contaminant is $CO_2$, $H_2O$, $H_2S$, $NO_x$ and/or $SO_x$.

It may be desirable to operate with a multiplicity of structure adsorbent beds containing the organosilica material-coated substrate, with several coupled in a heating/cooling operation and others involved in adsorption (and/or desorption). In such an operation, the adsorbent bed can be substantially cooled by a circulating heat transfer medium before it is switched into service for adsorption. One advantage of such an operation can be that the thermal energy used to swing the bed is retained in the heat transfer medium. If adsorption were to proceed simultaneously with cooling, then a substantial part of the heat in the bed could be lost to the adsorbate-free feed, and a higher heat load could be needed to restore the high temperature of the heat transfer medium.

Adsorptive kinetic separation (AKS) processes, as described above, are useful for development and production of hydrocarbons, such as gas and oil processing. Particularly, as described in U.S. Patent Application Publication No. 2013/032716, which is herein incorporated by reference in its entirety, the AKS processes described herein can use one or more kinetic swing adsorption process, such as pressure swing adsorption (PSA), thermal swing adsorption (TSA), calcination, and partial pressure swing or displacement purge adsorption (PPSA), including combinations of these processes; each swing adsorption process may be utilized with rapid cycles, such as using one or more rapid cycle pressure swing adsorption (RC-PSA) units, with one or more rapid cycle temperature swing adsorption (RC-TSA) units or with one or more rapid cycle partial pressure swing adsorption (RC-PPSA) units; exemplary kinetic swing adsorption processes are described in U.S. Pat. Nos. 7,959, 720; 8,545,602; 8,529,663; 8,444,750; and 8,529,662 and U.S. Provisional Application Nos. 61/448,121; 61/447,848; 61/447,869; and 61/447,877, which are each herein incorporated by reference in its entirety. The provided processes, can be useful for rapid, large scale, efficient separation of a variety of target gases from gas mixtures.

The provided processes and apparatuses may be used to prepare natural gas products by removing contaminants. The provided processes and apparatuses can be useful for preparing gaseous feed streams for use in utilities, including separation applications such as dew point control, sweetening/detoxification, corrosion protection/control, dehydration, heating value, conditioning, and purification. Examples of utilities that utilize one or more separation applications can include generation of fuel gas, seal gas, non-potable water, blanket gas, instrument and control gas, refrigerant, inert gas, and hydrocarbon recovery. Exemplary "not to exceed" product (or "target") acid gas removal specifications can include: (a) 2 vol % $CO_2$, 4 ppm $H_2S$; (b) 50 ppm $CO_2$, 4 ppm $H_2S$; or (c) 1.5 vol % $CO_2$, 2 ppm $H_2S$.

The provided processes and apparatuses may also be used to remove acid gas from hydrocarbon streams. Acid gas removal technology becomes increasingly important as remaining gas reserves exhibit higher concentrations of acid (sour) gas resources. Hydrocarbon feed streams can vary widely in amount of acid gas, such as from several parts per million to 90 vol %. Non-limiting examples of acid gas concentrations from exemplary gas reserves can include concentrations of at least: (a) 1 vol % $H_2S$, 5 vol % $CO_2$; (b) 1 vol % $H_2S$, 15 vol % $CO_2$; (c) 1 vol % $H_2S$, 60 vol % $CO_2$; (d) 15 vol % $H_2S$, 15 vol % $CO_2$; or (e) 15 vol % $H_2S$, 30 vol % $CO_2$.

One or more of the following may be utilized with the processes and apparatuses provided herein, to prepare a desirable product stream, while maintaining relatively high hydrocarbon recovery:

(a) removing acid gas with RC-TSA using advanced cycles and purges as described in U.S. Provisional Application No. 61/447,854, filed Mar. 1, 2011, as well as the U.S. Pat. No. 8,784,533, which are together incorporated by reference herein in their entirety;

(b) using a mesopore filler to reduce the amount of trapped methane in the adsorbent bed and increase the overall hydrocarbon recovery, as described in U.S. Pat. Nos. 7,959,720; 8,444,750; and 8,529,663, each of which is herein incorporated by reference in its entirety;

(c) depressurizing one or more RC-TSA units in multiple steps to intermediate pressures so that the acid gas exhaust can be captured at a higher average pressure, thereby decreasing the compression required for acid gas injection; pressure levels for the intermediate depressurization steps may be matched to the interstage pressures of the acid gas compressor to optimize the overall compression system;

(d) using exhaust or recycle streams to minimize processing and hydrocarbon losses, such as using exhaust streams from one or more RC-TSA units as fuel gas instead of re-injecting or venting;

(e) using multiple adsorbent particles in a single bed to remove trace amounts of first contaminants, such as $H_2S$, before removal of a second contaminant, such as $CO_2$; such segmented beds may provide rigorous acid gas removal down to ppm levels with RC-TSA units with minimal purge flow rates;

(f) using feed compression before one or more RC-TSA units to achieve a desired product purity;

(g) contemporaneous removal of non-acid gas contaminants such as mercaptans, COS, and BTEX; selection processes and materials to accomplish the same;

(h) selecting a cycle time and cycle steps based on adsorbent material kinetics; and (i) using a process and apparatus that uses, among other equipment, two RC-TSA units in series, wherein the first RC-TSA unit cleans a feed stream down to a desired product purity and the second RC-TSA unit cleans the exhaust from the first unit to capture methane and maintain high hydrocarbon recovery; use of this series design may reduce the need for a mesopore filler.

The processes, apparatuses, and systems provided herein can be useful in large gas treating facilities, such as facilities that process more than five million standard cubic feet per day (MSCFD) of natural gas, for example more than 15 MSCFD, more than 25 MSCFD, more than 50 MSCFD, more than 100 MSCFD, more than 500 MSCFD, more than one billion standard cubic feet per day (BSCFD), or more than two BSCFD.

V. FURTHER EMBODIMENTS

The invention can additionally or alternately include one or more of the following embodiments.

Embodiment 1

A method for coating a substrate, the method comprising:
(i) adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen atom bonded to a silicon atom of another compound and each $Z^2$ represents, a hydroxyl group, a $C_1$-$C_4$ alkoxy group, a $C_1$-$C_4$ alkyl group or an oxygen atom bonded to a silicon atom of another compound;
(ii) adding an adsorbent material to the solution to form a slurry;
(iii) coating the slurry onto a substrate;
(iv) aging the slurry; and
(v) drying the slurry to obtain a coating comprising the adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the substrate and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

Embodiment 2

The method of embodiment 1, wherein each $Z^1$ represents a $C_1$-$C_2$ alkoxy group.

Embodiment 3

The method of embodiment 1 or 2, wherein each $Z^2$ represents a $C_1$-$C_4$ alkoxy group.

Embodiment 4

The method of any one of the previous embodiments, wherein each $Z^2$ represents a $C_1$-$C_2$ alkoxy group.

Embodiment 5

The method of any one of the previous embodiments, wherein the at least one compound of Formula (Ia) is 1,1,3,3,5,5-hexaethoxy-1,3,5-trisilacyclohexane.

Embodiment 6

The method of any one of the previous embodiments, wherein each $Z^3$ represents a hydroxyl group, a $C_1$-$C_2$ alkoxy group, or an oxygen bonded to a silicon atom of another unit or an active site on the substrate, and $Z^4$ represents a hydroxyl group, a $C_1$-$C_2$ alkyl group, a $C_1$-$C_2$ alkoxy group, or an oxygen bonded to a silicon atom of another unit or an active site on the substrate.

Embodiment 7

The method of any one of the previous embodiments, wherein each $Z^3$ represents a hydroxyl group, ethoxy, or an oxygen bonded to a silicon atom of another unit or an active site on the substrate, and each $Z^4$ represents a hydroxyl group, ethoxy, or an oxygen bonded to a silicon atom of another unit or an active site on the substrate.

Embodiment 8

The method of any one of the previous embodiments, further comprising adding to the aqueous mixture at least a second compound selected from the group consisting of:
(i) a further compound of Formula (Ia);
(ii) a compound of Formula $R^1OR^2R^3R^4Si$ (II), wherein each $R^1$ represents a $C_1$-$C_4$ alkyl group; and $R^2$, $R^3$, and $R^4$ are each independently selected from the group consisting of a $C_1$-$C_4$ alkyl group, a $C_1$-$C_4$ alkoxy group, a nitrogen-containing $C_1$-$C_{10}$ alkyl group, a nitrogen-containing heteroalkyl group, and a nitrogen-containing optionally substituted heterocycloalkyl group;
(iii) a compound of Formula $Z^5Z^6Z^7Si$—R—$SiZ^5Z^6Z^7$ (III), wherein each $Z^5$ independently represents a $C_1$-$C_4$ alkoxy group; each $Z^6$ and $Z^7$ independently represent a $C_1$-$C_4$ alkoxy group or a $C_1$-$C_4$ alkyl group; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) a compound of Formula $M^1(OZ^8)_3$ (IV), wherein $M^1$ represents a Group 13 metal and each $Z^8$ independently represents a $C_1$-$C_6$ alkyl;
(v) a compound of Formula $(Z^9O))_2M^2$-O—$Si(OZ^{10})_3$ (V), wherein $M^2$ represents a Group 13 metal and $Z^9$ and $Z^{10}$ each independently represent a $C_1$-$C_6$ alkyl; and
(vi) a cyclic compound of Formula

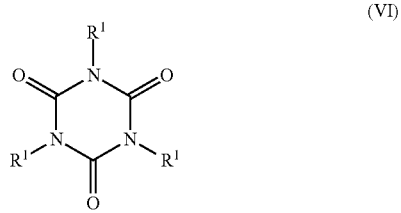

(VI)

wherein each $R^1$ independently is a $X^1OX^2X^3SiX^4$ group, wherein each $X^1$ represents a $C_1$-$C_4$ alkyl group; $X^2$ and $X^3$ each independently represent a $C_1$-$C_4$ alkyl group, a $C_1$-$C_4$ alkoxy group; and $X^4$ represents a $C_1$-$C_8$ alkylene group bonded to a nitrogen atom of the cyclic compound; and
(vii) a combination thereof.

Embodiment 9

The method of embodiment 8, wherein the second compound is a compound of Formula (Ia), wherein each $Z^1$ represents a $C_1$-$C_2$ alkoxy group and $Z^2$ represents $C_1$-$C_2$ alkoxy group or a $C_1$-$C_2$ alkyl group.

Embodiment 10

The method of embodiment 9, wherein the compound of Formula (Ia) is 1,3,5-trimethyl-1,3,5-triethoxy-1,3,5-trisilacyclohexane.

Embodiment 11

The method of any one of embodiments 8-10, wherein the second compound is a compound of Formula (II), wherein each $R^1$ represents a $C_1$-$C_2$ alkyl group and $R^2$, $R^3$, and $R^4$ are each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

Embodiment 12

The method of embodiment 11, wherein the compound of Formula (II) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysilyl)ethyl)pyridine, 1-(3-(triethoxysilyl)propyl)-4,5-dihydro-1H-imidazole, and (3-aminopropyl)triethoxysilane.

Embodiment 13

The method of any one of embodiments 8-12, wherein the second compound is a compound of Formula (III), wherein each $Z^5$ represents a $C_1$-$C_2$ alkoxy group; each $Z^6$ and $Z^7$ independently represent a $C_1$-$C_2$ alkoxy group, or a $C_1$-$C_2$ alkyl group; and R is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

Embodiment 14

The method of embodiment 13, wherein the compound of Formula (III) is selected from the group consisting of 1,2-bis(methyldiethoxysilyl)ethane, bis(triethoxysilyl)methane, 1,2-bis-(triethoxysilyl)ethylene, N,N'-bis[(3-trimethoxysilyl)propyl]ethylenediamine, bis[(methyl-diethoxysilyl)propyl]amine, and bis[(methyldimethoxysilyl)propyl]-N-methylamine.

Embodiment 15

The method of any one of embodiments 8-14, wherein the second compound is a compound of Formula (IV), wherein $M^1$ is Al or B and each $Z^8$ represents a $C_1$-$C_4$ alkyl group.

Embodiment 16

The method of any one of embodiments 8-15, wherein the second compound is a compound of Formula (V), wherein $M^2$ is Al or B; and $Z^9$ and $Z^{10}$ each independently represent a $C_1$-$C_4$ alkyl group.

Embodiment 17

The method of embodiment 8 or 15, wherein the second compound is selected from the group consisting of aluminum trimethoxide, aluminum triethoxide, aluminum isopropoxide, and aluminum-tri-sec-butoxide.

Embodiment 18

The method of any one of embodiments 8-17, wherein the second compound is a compound of Formula (VI), wherein each $X^1$ represents a $C_1$-$C_2$ alkyl group; $X^2$ and $X^3$ each independently represent a $C_1$-$C_2$ alkyl group or a $C_1$-$C_2$ alkoxy group; and each $X^4$ represents a $C_1$-$C_4$ alkylene group bonded to a nitrogen atom of the cyclic compound.

Embodiment 19

The method of embodiment 18, wherein the compound of Formula (VI) is tris(3-trimethoxysilylpropyl)isocyanurate.

Embodiment 20

The method of any one of the previous embodiments, wherein the aqueous mixture comprises a base and has a pH from about 8 to about 15.

Embodiment 21

The method of embodiment 20, wherein the base is ammonium hydroxide or a metal hydroxide.

Embodiment 22

The method of any one of the previous embodiments, wherein the aqueous mixture comprises an acid and has a pH from about 0.01 to about 6.0.

Embodiment 23

The method of embodiment 22, wherein the acid is an inorganic acid.

Embodiment 24

The method of embodiment 23, wherein the inorganic acid is hydrochloric acid.

Embodiment 25

The method of any one of the previous embodiments, wherein the slurry is aged in step (d) for up to 24 hours at a temperature of about 20° C. to about 125° C.

Embodiment 26

The method of any one of the previous embodiments, wherein the slurry is dried at a temperature of about 70° C. to about 150° C.

Embodiment 27

The method of any one of the previous embodiments, wherein step (c) is repeated one or more times to produce a thicker coating.

Embodiment 28

The method of any one of the previous embodiments further comprising pre-treating the substrate.

Embodiment 29

The method of embodiment 28, wherein pre-treating the substrate comprises applying a solution comprising an oxidizing agent and, optionally an inorganic acid to the substrate.

Embodiment 30

The method of embodiment 29, wherein the oxidizing agent is hydrogen peroxide.

Embodiment 31

The method of embodiment 29 or 30, wherein the inorganic acid is sulfuric acid.

Embodiment 32

The method of any one of the previous embodiments, wherein the organosilica material has an average pore diameter of about 2.0 nm to about 25.0 nm.

Embodiment 33

The method of any one of the previous embodiments, wherein the organosilica material has a surface area of about 200 $m^2$/g to about 2500 $m^2$/g.

Embodiment 34

The method of any one of the previous embodiments, wherein the organosilica material has a pore volume of 0.1 $cm^3$/g about 3.0 $cm^3$/g.

Embodiment 35

The method of any one of the previous embodiments further comprising agitating the slurry before coating.

Embodiment 36

The method of any one of the previous embodiments, wherein the adsorbent material is selected from the group consisting of a microporous adsorbent material, a mesoporous adsorbent material, an analogous periodic mesoporous adsorbent material, a metal oxide, a carbon, and a combination thereof.

Embodiment 37

The method of any one of the previous embodiments, wherein the adsorbent material is a zeolite.

Embodiment 38

The method of embodiment 37, wherein the zeolite is selected from the group consisting of a cationic form of zeolite A, Y, dealuminized Y, or Linde L; chabazite; erionite; mordenite; zeolite Beta; a ZSM-type zeolite; MCM-22; MCM-49; Nu-87; UTD-1; CIT-5; EMC-2; and Cloverite.

Embodiment 39

The method of any one of the previous embodiments, wherein the solution is stirred for at least 18 hours before adding the adsorbent material.

Embodiment 40

The method of any one of the previous embodiments further comprising adding a $C_1$-$C_4$ alcohol to the solution.

Embodiment 41

The method of embodiment 40, wherein the $C_1$-$C_4$ alcohol is ethanol.

Embodiment 42

The method of any one of the previous embodiments further comprising adding an additional amount of the compound of Formula (Ia) to the slurry.

Embodiment 43

The method of embodiment 42, wherein the compound of Formula (Ia) is 1,1,3,3,5,5-hexaethoxy-1,3,5-trisilacyclohexane.

Embodiment 44

The method of any one of the previous embodiments further comprising supplying a purge gas to the substrate after coating.

Embodiment 45

The method of embodiment 44, wherein the purge gas is an inert gas.

Embodiment 46

The method of embodiment 45, wherein the inert gas is nitrogen.

Embodiment 47

The method of any one of the previous embodiments, wherein the substrate is selected from the group consisting of a capillary tube, a microchannel, a monolith, a spherical silica particle and a silicon wafer.

Embodiment 48

The method of any one of the previous embodiments, wherein the method does not comprise a calcination step.

Embodiment 49

The method of any one of the previous embodiments, wherein the coating has a thickness of up to about 150 μm.

Embodiment 50

The method of any one of the previous embodiments, wherein the coating comprises about 1% to about 50% organosilica material as a binder.

Embodiment 51

An organosilica material-coated substrate made according to the method of any one of the previous embodiments.

Embodiment 52

The organosilica material-coated substrate of embodiment 51 for use in chromatography.

Embodiment 53

The organosilica material-coated substrate of embodiment 51 or 52 for use in gas, liquid or supercritical chromatography.

Embodiment 54

A gas separation process comprising contacting a gas mixture comprising $CH_4$ and at least one contaminant selected from the group consisting $CO_2$, $H_2O$, $H_2S$, $NO_x$, and $SO_x$ with the organosilica material-coated substrate of embodiment 51.

Embodiment 55

The gas separation process of embodiment 54, wherein the process comprises PSA, TSA, PPSA, PTSA, RCPSA, RCTSA, RCPPSA or RCPTSA.

EXAMPLES

The following examples are merely illustrative, and do not limit this disclosure in any way.

Example 1

Capillary Column Coating Experiments

Below is the procedure used for coating quartz capillary columns (25 cm long×530 μm inside diameter) obtained from Sigma-Aldrich (uncoated chromatography columns) with an organosilica material binder and zeolitic material:

1. Treated Column: The column was pretreated with a solution made with 30 wt % hydrogen peroxide and 48 wt % sulfuric acid (1:1 ratio in weight). The capillary tube was filled with the solution for 30 minutes, then washed with deionized (DI) water. Then column was dried in a vacuum oven at 120° C. overnight (16-24 hr) before coating with zeolites.
2. Made Solution: 6.23 g 30% $NH_4OH$ was mixed with 7.92 g DI water to make an aqueous mixture. 1 g (alternatively up 4 g can be added) 1,1,3,3,5,5-hexaethoxy-1,3,5-Trisilacyclohexane ("reagent 1") was added into the above aqueous mixture to make a mesoporous organosilica (MO) solution. The solution was then stirred for 1 day (24-30 hours) at room temperature (15° C.-25° C.). Then ethanol was added to the above solution with weight ratio of 1:1 MO solution:ethanol (wt:wt).
3. Added Zeolite or Silica to Make a Slurry: 0.78 g zeolites were added into 2 g of the above MO solution to form a zeolite/MO slurry or silica/MO slurry. The slurry was sonicated for 10 minutes. Then 3.0 g reagent 1 was added into the slurry. The slurry was stirred for 1 day (24-30 hours) at room temperature (15° C.-25° C.).
4. Coated the Columns: A high pressure nitrogen (35 KPa) stream was used to fill the treated columns with the zeolite/MO slurry or silica/MO slurry. The high pressure nitrogen purge continued for at least 5 minutes. The coated column was kept at room temperature for 1 day (24-30 hours) to let the MO binder cure. Then the column was transferred to an oven and treated at 70° C. to 75° C. for 6 hours. Then the column was dried at 120° C. under vacuum overnight (16-24 hr).

5. In some instances, multiple coatings were applied by repeating step 4.

The above procedure was repeated using different amounts of reagent 1 and different zeolites or silicas to create different zeolite/MO and silica/MO slurries according to Table 1 below. In Table 1, Zeolites 3A, 4A, 5A and 13X and Silica Gel (100-200 μm particulates) were obtained from Sigma-Aldrich (St Louis, Mo.). The Silica Gel (5 μm spheres) were obtained from SORBTECH (Norcross, Ga.). FIGS. 1-9 show SEM images of the coatings on the capillary columns for each of the zeolite/MO and silica/MO slurries. In each repetition, a 25 cm long×530 micron inside diameter quartz capillary tube was used (Sigma-Aldrich uncoated chromatography column) except in FIG. 5 where 100 cm long capillary columns were used. DDR (~10 μm diameter crystals of high SiO2 [Si]ZSM-58) prepared as described in for example U.S. Patent Publication No. 2014/0157986.

TABLE 1

| Sample | FIG. | Amount of Reagent 1 (g) | Zeolite or Silica | Amount of coating on column (mg) | Thickness of coating (μm) |
|---|---|---|---|---|---|
| Coating 1 | 1a-1b | 4 | 13X (1 μm sized particles) | 3 | 10 |
| Coating 2 | 2a-2b | 4 | 3A | 5 | 15 |
| Coating 3 | 3a-3b | 4 | 4A | 4 | 12 |
| Coating 4 | 4a-4b | 4 | 5A | 13 | 28 |
| Coating 5* | 5a-5d | 1 | 13X | 7 | 7 |
| Coating 6** | 6a-6b | 2 | DDR(10 μm sized particles) | 7.6 | 20 |
| Coating 7 | 7a-7b | 2 | Silica Gel (100-200 μm particulates) | 7.2 | 100 |
| Coating 8 | 8a-8b | 1 | Silica Gel (5 μm spheres) | 3.2 | 15 |
| Coating 9*** | 9a-9f | 2 | 5A | 7 | 30 |

*For Coating 5, 100 cm long capillary column was used instead of 25 cm long capillary column.
**For Coating 6, 1.54 g of MO solution was used instead of 2 g.
***For Coating 9, two coats of the zeolite/MO slurry were applied to the capillary column.

The above tested Coatings 1-9 showed uniform coverage and good quality.

Example 2

Adhesion Quality of Zeolite/MO Coating

In order to test adhesion quality of the zeolite/MO coating on the surface of the capillary columns, high velocity nitrogen (40-50 SCFH) was used to purge the capillary columns overnight (16-24 hr) for Coatings 2 and 3. Experimental data showed that there was an initial 16 wt % minimal loss of coating, with little additional loss, indicating good adhesion quality of the zeolite/MO coating on the surface of the capillary columns. FIGS. 10 and 11 are SEM images of the coatings before/after high velocity nitrogen purge while FIG. 12 shows the same procedure on a capillary column coated with a traditional silica binder (coating method was the same, except replacing MO binder with colloidal silica) (Comparative Coating A). The images in FIGS. 10 and 11 show the MO bound coatings were stable following the nitrogen purge. FIG. 12 clearly cause damage and loss of the coating with traditional silica binder.

Example 3

Zeolite/MO Coating on Large Surfaces

3A. Zeolite/MO Coating on SiO$_2$/Si Wafer

An aqueous mixture of 6.23 g 30% NH$_4$OH and 7.92 g DI water was made; then 2 g 1,1,3,3,5,5-hexaethoxy-1,3,5-Trisilacyclohexane ("reagent 1") was added to the aqueous mixture to form a MO solution, and the MO solution was stirred for 1 day (24-30 hours) at room temperature (15° C.-25° C.). Ethanol was added to the MO solution with weight ratio of 1:1. A zeolite/MO slurry was made with 0.78 g 13X molecular sieve and 2 g MO solution. The zeolite/MO slurry was sonicated for 10 minutes. Then the 13X/MO slurry was washcoated on a SiO$_2$/Si wafer to obtain Coating 10. The coated wafer (Coating 10) was cured and dried according to Example 1. SEM analysis confirmed the high quality of Coating 10 as shown in the SEM images in FIG. 13.

3B. Zeolite/MO Coating on the Channel Surface of a Monolith

Using the same method as in Example 3A, a13X/MO slurry was coated on a channel surface of a monolith to obtain Coating 11. N$_2$ was used to blow off the excess slurry on the surface of the channels. The coated monolith was kept at room temperature for 1 day to let the 13X/MO binder cure. The coated monolith (Coating 11) was cured and dried according to Example 1. SEM analysis confirmed the high quality of Coating 11 as shown in the SEM images in FIG. 14. The thickness of the coating was about 22 microns.

Example 4

Dehydration Using MO/Zeolite Coating

Figure 1B:
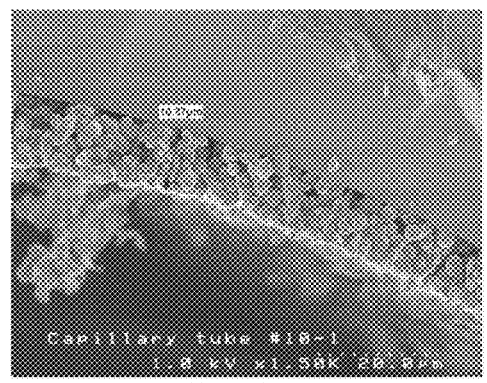
FIG. 1b illustrates a SEM image of a more magnified view of a cross-section of Coating 1 on a capillary column.
Figure 2A:
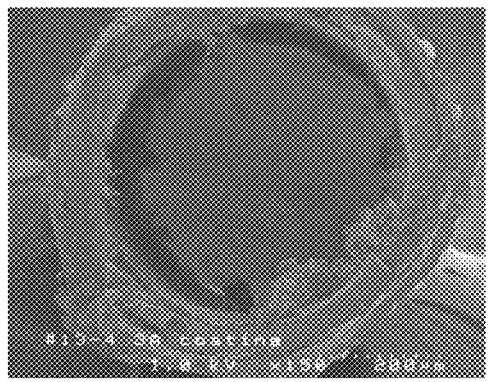
FIG. 2a illustrates a SEM image of a cross-section of Coating 2 on a capillary column.
Figure 2B:
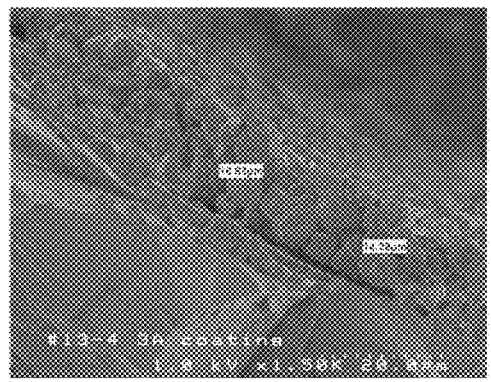
FIG. 2b illustrates a SEM image of a more magnified view of a cross-section of Coating 2 on a capillary column.
Figure 3A:
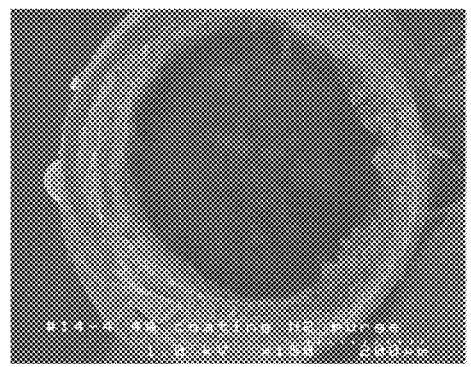
FIG. 3a illustrates a SEM image of a cross-section of Coating 3 on a capillary column.
Figure 3B:
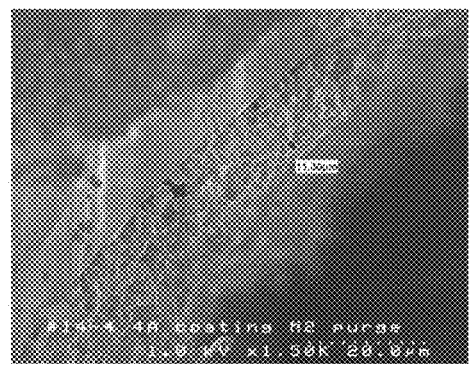
FIG. 3b illustrates a SEM image of a more magnified view of a cross-section of Coating 3 on a capillary column.
Figure 4A:
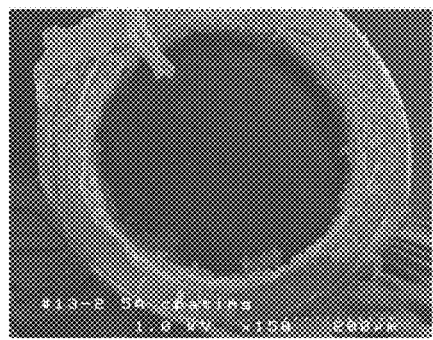
FIG. 4a illustrates a SEM image of a cross-section of Coating 4 on a capillary column.
Figure 4B:
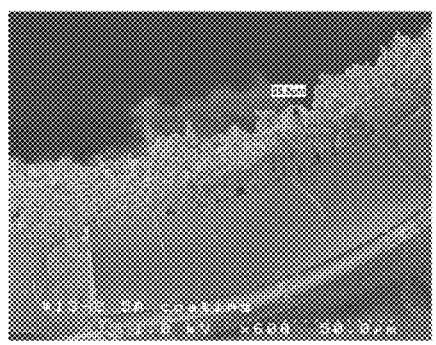
FIG. 4b illustrates a SEM image of a more magnified view of a cross-section of Coating 4 on a capillary column.
Figure 5A:
FIG. 5a illustrates a SEM image of a cross-section of Coating 5 on a capillary column.
Figure 5B:
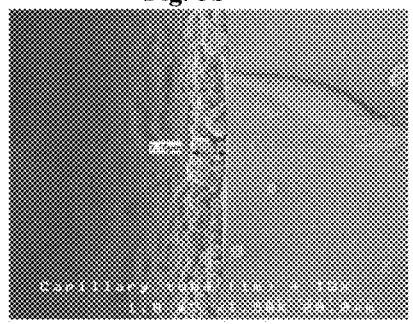
FIG. 5b illustrates a SEM image of another view of a cross-section of Coating 5 on a capillary column.
Figure 5C:
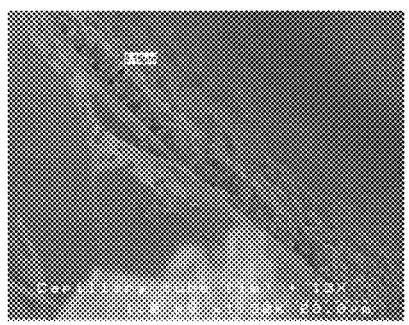
FIG. 5c illustrates a SEM image of another view of a cross-section of Coating 5 on a capillary column.
Figure 5D:
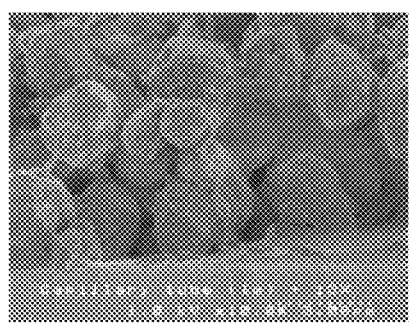
FIG. 5d illustrates a SEM image of a more magnified view of a cross-section of Coating 5 on a capillary column.
Figure 6A:
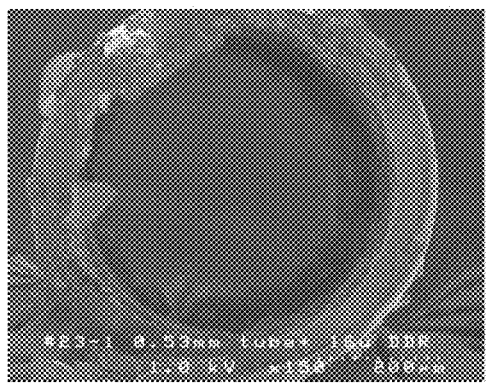
FIG. 6a illustrates a SEM image of a cross-section of Coating 6 on a capillary column.
Figure 6B:
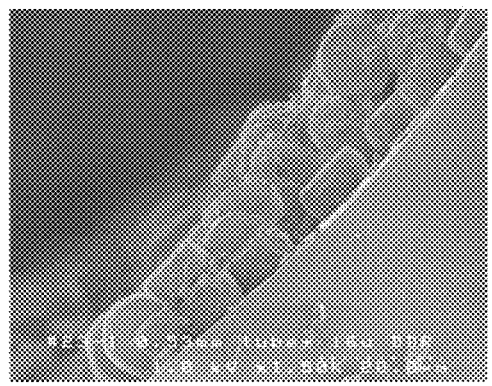
FIG. 6b illustrates a SEM image of a more magnified view of a cross-section of Coating 6 on a capillary column.
Figure 7A:
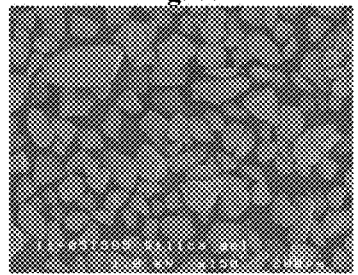
FIG. 7a illustrates a SEM image of a more magnified view of Coating 7 on a capillary column.
Figure 7B:
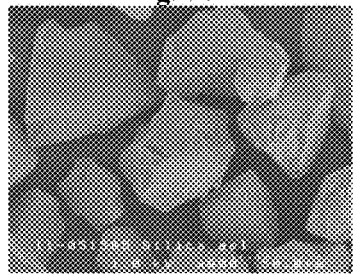
FIG. 7b illustrates a SEM image of another more magnified view of Coating 7 on a capillary column.
Figure 7C:
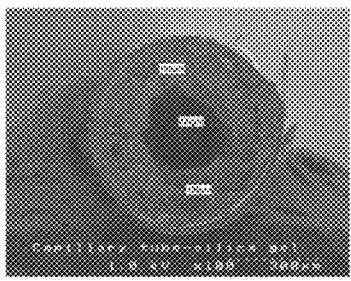
FIG. 7c illustrates a SEM of a cross-section of Coating 7 on a capillary.
Figure 7D:
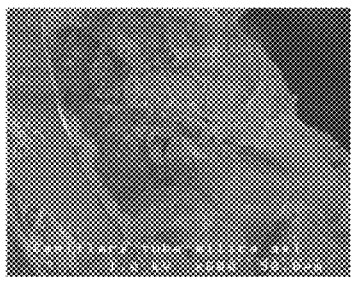
FIG. 7d illustrates a SEM image of a more magnified view of a cross-section of Coating 7 on a capillary column.
Figure 7E:
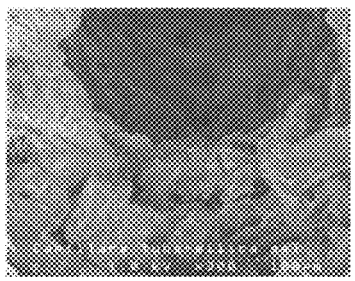
FIG. 7e illustrates a SEM image of another more magnified view of a cross-section of Coating 7 on a capillary column.
Figure 8A:
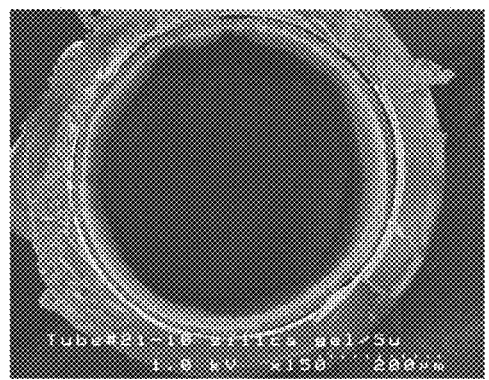
FIG. 8a illustrates a SEM image of a cross-section of Coating 8 on a capillary column.
Figure 8B:
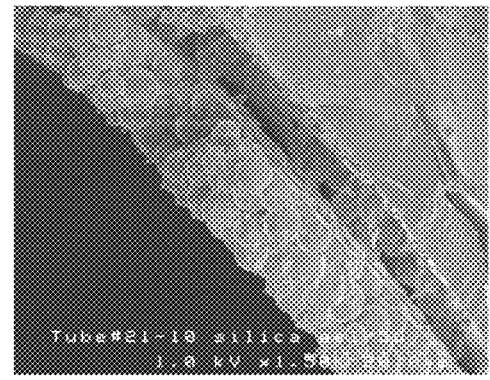
FIG. 8b illustrates a SEM image of a more magnified view of a cross-section of Coating 8 on a capillary column.
Figure 12A:
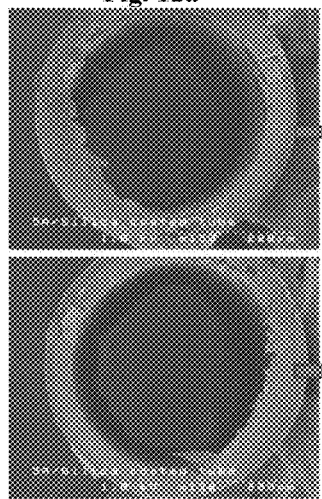
FIG. 12a-12f illustrate SEM images of cross-section views of Comparative Coating A on a capillary column after a high velocity $N_2$ purge.
Figure 12B:
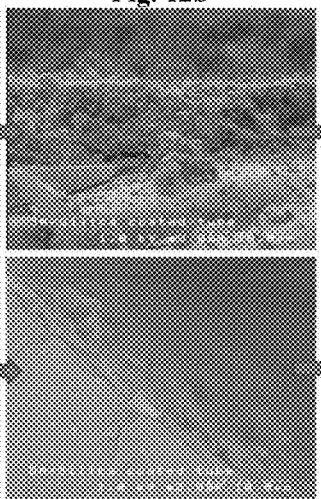
Figure 12C:
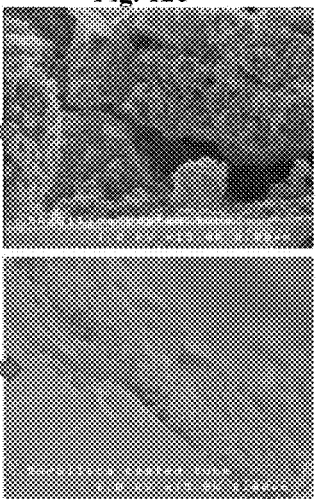
Figure 12D:
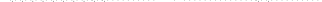
Figure 12E:
Figure 12F:
Figure 13A:
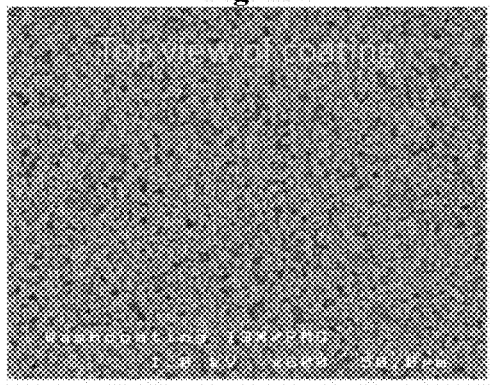
FIG. 13a illustrates SEM images of a topview of Coating 10 on a $SiO_2$/Si wafer.
Figure 13B:
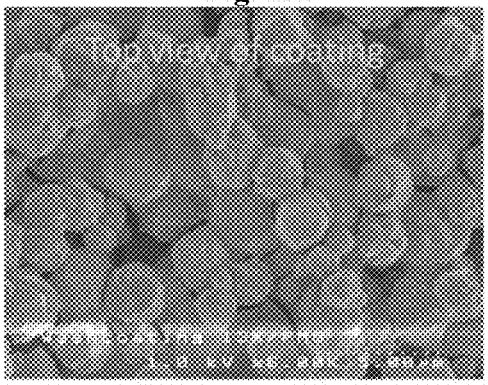
FIG. 13b illustrates SEM images of a more magnified topview of Coating 10 on a $SiO_2$/Si wafer.
Figure 13C:
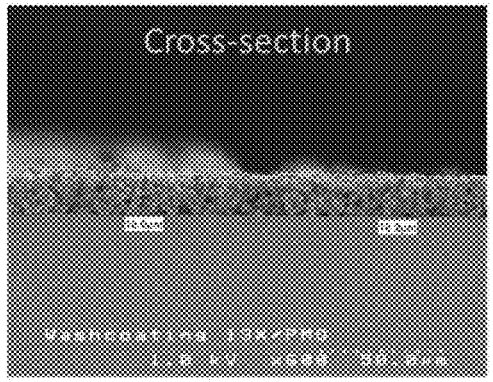
FIG. 13c illustrates SEM images of a cross-section of Coating 10 on a $SiO_2$/Si wafer.
Figure 13D:
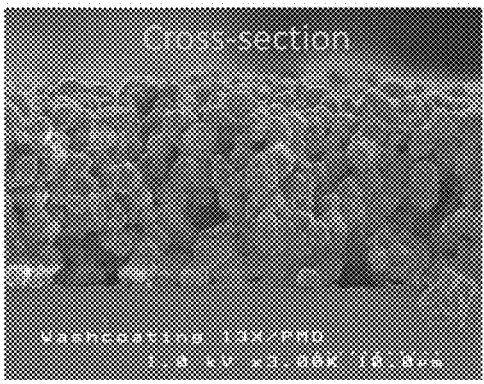
Figure 14A:
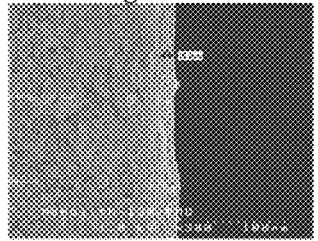
FIGS. 14a-14f illustrate SEM images of view of Coating 11 on a monolith surface.
Figure 14B:
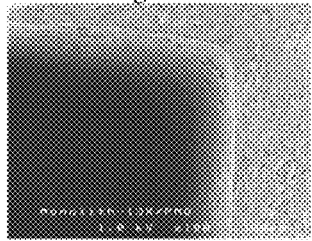
Figure 14C:
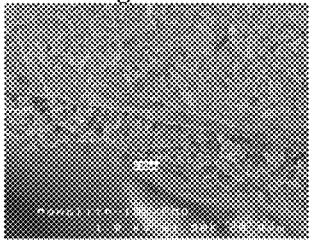
Figure 14D:
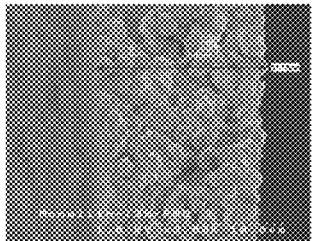
Figure 14E:
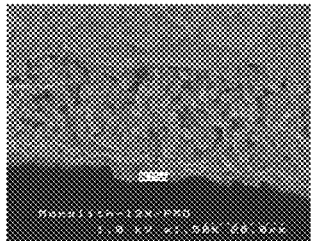
Figure 14F:
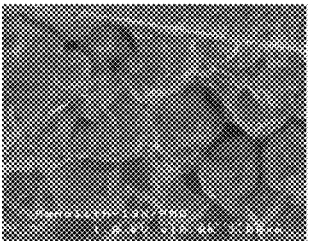

Coating 1 as shown in FIGS. 1a and 1b was evaluated for removing water vapor from a gas stream. A single capillary column was mounted with epoxy sealant in a 0.25 inch outside diameter×0.035" wall thickness 7 inch long 316 stainless steel tube, to facilitate handling in the test unit. After mounting the ends of the 530 micron capillary were cut off to final length of about 180 mm. The zeolite coating weight used was therefore about 2 mg. Prior to use, the column was purged with dry nitrogen at 500 cc/min for several hours at about 23° C. and atmospheric pressure (1 atm).

Figure 15:
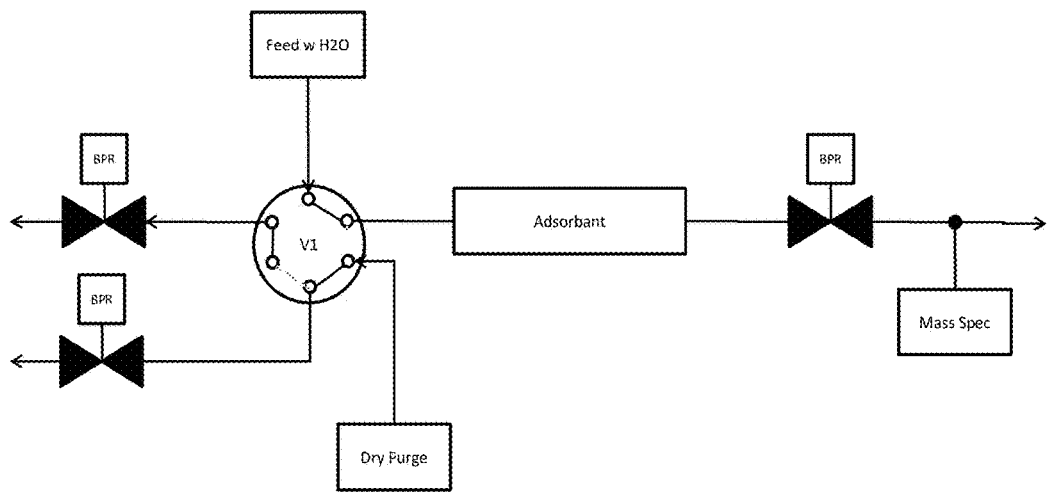
FIG. 15 illustrates a schematic for a test unit used to test removal of water vapor from a gas stream using Coating 1 on a capillary column.

The test unit used is shown schematically in FIG. 15. Nitrogen feed gas with 10% helium tracer, typically flowing at 500-1500 sccm, was saturated with water by passing through a bubbler maintained at 600 psig and ambient temperature of about 25° C. The water saturated gas stream was reduced in pressure to 400 psig (or 200 psig, as noted) while passing through heated tubing resulting in a feed gas containing about 600 ppm water vapor. The feed gas was directed through a multiport valve to the adsorbent capillary column, which in the following examples was operated at ambient temperature of 25° C. The gas exiting the adsorbent capillary was continuously sampled by means of mass spectrometer, after passing through the back-pressure regulator (BPR). The adsorption capacity of the adsorbent was determined from the water breakthrough curve. Multiple cycles were achieved by purging the adsorbent tube with dry nitrogen (no helium tracer) supplied at the desired pressure by switching the multiport valve, and then repeating the adsorption process. The purging process was accelerated by decreasing the operating pressure to 20 psig, followed by rapid repressurization for the adsorption step, as is typical in Pressure Swing Processes (PSA).

Figure 16:
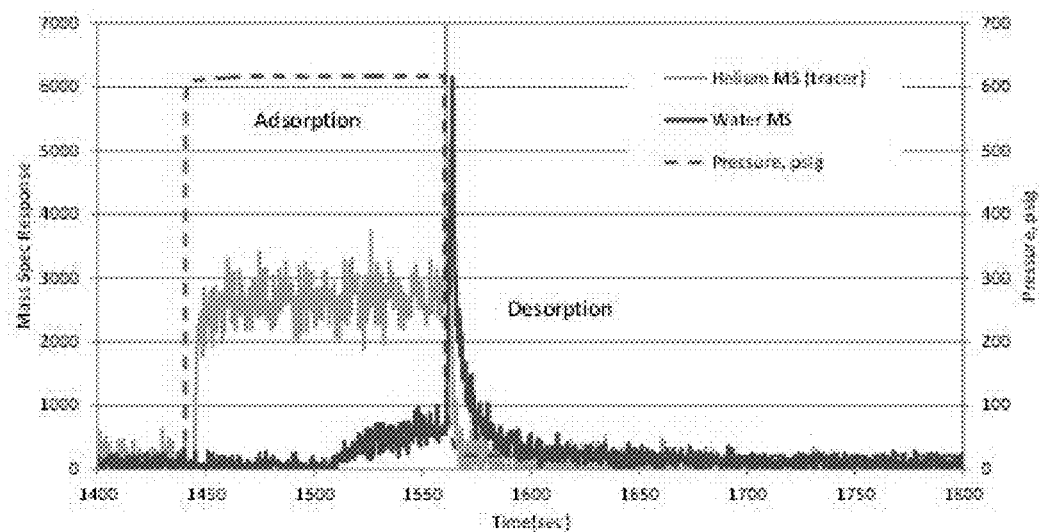
FIG. 16 illustrates the results of a PSA cycle using Coating 1 on a capillary column to dehydrate a gas stream at 600 psig.
Figure 17:
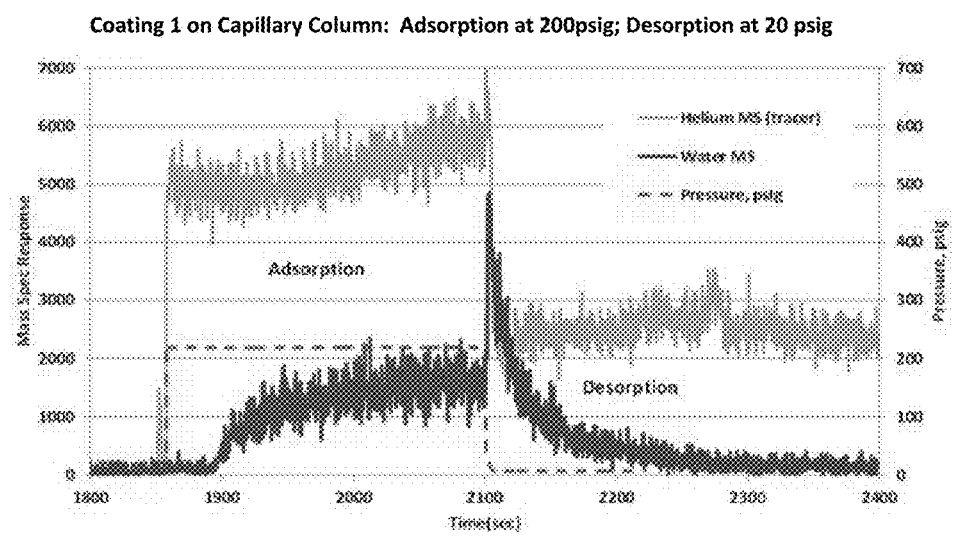
FIG. 17 illustrates the results of a PSA cycle using Coating 1 on a capillary column to dehydrate a gas stream at 200 psig.

Coating 1 was found to be effective for adsorption of water vapor at the conditions noted. Representative results are shown in FIGS. 16 and 17 and described below.

Several initial runs were made at 200 psig feed pressure and 500 cc/min nitrogen with 10% helium tracer and 630 ppm water vapor (590 psig bubbler) to establish the pressure swing procedures. During this time the adsorbent was exposed to four 300 second adsorption and corresponding 300 second desorption cycles. Desorption of water from the zeolite was achieved by depressurization to about 20 psig, with 500 cc/min dry nitrogen containing no helium tracer. Forward flow was maintained throughout the run. A total of 127 mmol of water/g 13X adsorbent was processed in this time frame, far in excess of the 13X zeolites water adsorption capacity of about 19.4 mmol/g (Water capacity for calcined NaX estimated to be 0.35 g/g at 20 torr, 298K from D. W. Breck, Zeolite Molecular Sieves, Wiley-Interscience, 1974, p. 601 Isotherm).

The pressure and flowrate were increased to 600 psig and 1500 cc/min water saturated nitrogen (620 psig) with 10% helium tracer for adsorption and 20 psig with 1500 cc/min dry nitrogen for desorption. Several additional experiments were conducted demonstrating that the PSA procedures were effective at these conditions, Forward flow was maintained throughout run (not back flushed). FIG. 16 illustrates the results of a typical and repeatable PSA cycle at these conditions, with an adsorption time of 120 seconds, and a desorption time of 300 seconds. Water breakthrough occurred about 60 seconds after the pressure swing to 600 psig, with the initial time based on the helium tracer signal. This corresponded to 18.6 mmol water adsorbed/g 13X zeolite, in agreement with the expected capacity of the adsorbent. The dehumidified gas water concentration corresponded to about 50 ppmv at breakthrough. A corrected value based on the background MS signal was also calculated, corresponding to 15.7 mmol/g, well within the expected errors of measurement, given the very low mass of the zeolite coating (2 mg). Decreasing the pressure for desorption to 20 psig resulted in a substantial increase in the water signal initially, followed by a return to the background water signal after 300 seconds. The conditions of this test were relatively severe, with gas velocities of 3.0 m/s during adsorption and up to about 50 m/s during desorption, without a noticeable loss in performance.

Following this run, the pressure was decreased to 200 psig for the adsorption cycle, with lower 500 cc/min nitrogen flows. The adsorption cycle was extended to 240 sec to achieve complete saturation of the adsorbent. The PSA desorption step remained at 20 psig 300 sec. FIG. 17 illustrates the results. Again, the water adsorbed, 4.5 mmol/g 13X, was calculated at the time of breakthrough (not at total saturation), to estimate working capacity. The dehumidified gas water concentration corresponded to about 50 ppmv at breakthrough. A corrected value based on the background MS signal was also calculated, corresponding to 4.1 mmol/g, well within the expected errors of measurement, especially considering the limited amount of adsorbent used at 2 mg. Decreasing the pressure for desorption to 20 psig resulted in a substantial increase in the water signal initially, followed by a return to the background water signal after 300 seconds. Again, the conditions of this test were relatively severe, with gas velocities of 2.9 m/s during adsorption step and up to about 18 m/s during desorption.

A summary of the results are provided in Table 2 below. As stated above, 13X zeolites has water adsorption capacity of about 19.4 mmol/g.

TABLE 2

|  | High Pressure | Low Pressure |
|---|---|---|
| Temperature (° C.) | 25 | 25 |
| Adsorption Pressure (psig) | 609 | 218 |
| Gas Rates (cc/min) | 1500 | 500 |
| Water Concentration (ppmv) | 609 | 630 |
| Adsorption Capacity (mmol/g) | 18.6 | 4.5 |
| Water at Breakthrough (ppmv) | ~50 | ~50 |
| Gas Velocity Adsorption (m/s) | 3.0 | 2.9 |
| Gas Velocity Desorption (m/s) | 53.6 | 17.9 |

What is claimed is:

1. A method for coating a substrate, the method comprising:
   (a) adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen atom bonded to a silicon atom of another compound and each $Z^2$ represents, a hydroxyl group, a $C_1$-$C_4$ alkoxy group, a $C_1$-$C_4$ alkyl group or an oxygen atom bonded to a silicon atom of another compound;
   (b) adding an adsorbent material to the solution to form a slurry;
   (c) coating the slurry onto a substrate;
   (d) aging the slurry; and
   (e) drying the slurry to obtain a coating comprising the adsorbent material and a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the substrate and each $Z^4$ represents a hydroxyl group, a $C_1$-$C_4$ alkoxy group, a $C_1$-$C_4$ alkyl group, an oxygen atom bonded to a silicon atom of another unit or an active site on the substrate.

2. The method of claim 1, wherein each $Z^1$ represents a $C_1$-$C_2$ alkoxy group.

3. The method of claim 2, wherein each $Z^2$ represents a $C_1$-$C_4$ alkoxy group.

4. The method of claim 3, wherein each $Z^2$ represents a $C_1$-$C_2$ alkoxy group.

5. The method of claim 1, wherein the at least one compound of Formula (Ia) is 1,1,3,3,5,5-hexaethoxy-1,3,5-trisilacyclohexane.

6. The method of claim 1, wherein each $Z^3$ represents a hydroxyl group, a $C_1$-$C_2$ alkoxy group, or an oxygen bonded to a silicon atom of another unit or an active site on the substrate, and $Z^4$ represents a hydroxyl group, a $C_1$-$C_2$ alkyl group, a $C_1$-$C_2$ alkoxy group, or an oxygen bonded to a silicon atom of another unit or an active site on the substrate.

7. The method of claim 6, wherein each $Z^3$ represents a hydroxyl group, ethoxy, or an oxygen bonded to a silicon atom of another unit or an active site on the substrate, and each $Z^4$ represents a hydroxyl group, ethoxy, or an oxygen bonded to a silicon atom of another unit or an active site on the substrate.

8. The method of claim 1, further comprising adding to the aqueous mixture at least a second compound selected from the group consisting of:
(i) a further compound of Formula (Ia);
(ii) a compound of Formula $R^1OR^2R^3R^4Si$ (II), wherein each $R^1$ represents a $C_1$-$C_4$ alkyl group; and $R^2$, $R^3$, and $R^4$ are each independently selected from the group consisting of a $C_1$-$C_4$ alkyl group, a $C_1$-$C_4$ alkoxy group, a nitrogen-containing $C_1$-$C_{10}$ alkyl group, a nitrogen-containing heteroalkyl group, and a nitrogen-containing optionally substituted heterocycloalkyl group;
(iii) a compound of Formula $Z^5Z^6Z^7Si$—R—$SiZ^5Z^6Z^7$ (III), wherein each $Z^5$ independently represents a $C_1$-$C_4$ alkoxy group; each $Z^6$ and $Z^7$ independently represent a $C_1$-$C_4$ alkoxy group or a $C_1$-$C_4$ alkyl group; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) a compound of Formula $M^1(OZ^8)_3$ (IV), wherein $M^1$ represents a Group 13 metal and each $Z^8$ independently represents a $C_1$-$C_6$ alkyl;
(v) a compound of Formula $(Z^9O)_2M^2$-O—$Si(OZ^{10})_3$ (V), wherein $M^2$ represents a Group 13 metal and $Z^9$ and $Z^{10}$ each independently represent a $C_1$-$C_6$ alkyl group; and
(vi) a cyclic compound of Formula

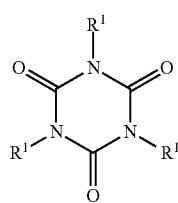

(VI)

wherein each $R^1$ independently is a $X^1OX^2X^3SiX^4$ group, wherein each $X^1$ represents a $C_1$-$C_4$ alkyl group; $X^2$ and $X^3$ each independently represent a $C_1$-$C_4$ alkyl group, a $C_1$-$C_4$ alkoxy group; and $X^4$ represents a $C_1$-$C_8$ alkylene group bonded to a nitrogen atom of the cyclic compound; and
(vii) a combination thereof.

9. The method of claim 8, wherein are the second compound is a compound of Formula (Ia), wherein each $Z^1$ represents a $C_1$-$C_2$ alkoxy group and $Z^2$ represents $C_1$-$C_2$ alkoxy group or a $C_1$-$C_2$ alkyl group.

10. The method of claim 9, wherein the compound of Formula (Ia) is 1,3,5-trimethyl-1,3,5-triethoxy-1,3,5-trisilacyclohexane.

11. The method of claim 8, wherein the second compound is a compound of Formula (II), wherein each $R^1$ represents a $C_1$-$C_2$ alkyl group and $R^2$, $R^3$, and $R^4$ are each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

12. The method of claim 11, wherein the compound of Formula (II) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysilyl)ethyl)pyridine, 1-(3-(triethoxysilyl)propyl)-4,5-dihydro-1H-imidazole, and (3-aminopropyl)triethoxysilane.

13. The method of claim 8, wherein the second compound is a compound of Formula (III), wherein each $Z^5$ represents a $C_1$-$C_2$ alkoxy group; each $Z^6$ and $Z^7$ independently represent a $C_1$-$C_2$ alkoxy group, or a $C_1$-$C_2$ alkyl group; and R is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

14. The method of claim 13, wherein the compound of Formula (III) is selected from the group consisting of 1,2-bis(methyldiethoxysilyl)ethane, bis(triethoxysilyl)methane, 1,2-bis-(triethoxysilyl)ethylene, N,N'-bis[(3-trimethoxysilyl)propyl]ethylenediamine, bis[(methyl-diethoxysilyl)propyl]amine, and bis[(methyldimethoxysilyl)propyl]-N-methylamine.

15. The method of claim 8, the second compound is a compound of Formula (IV), wherein $M^1$ is Al or B and each $Z^8$ represents a $C_1$-$C_4$ alkyl group.

16. The method of claim 8, the second compound is a compound of Formula (V), wherein $M^2$ is Al or B; and $Z^9$ and $Z^{10}$ each independently represent a $C_1$-$C_4$ alkyl group.

17. The method of claim 15, wherein the second compound is selected from the group consisting of aluminum trimethoxide, aluminum triethoxide, aluminum isopropoxide, and aluminum-tri-sec-butoxide.

18. The method of claim 8, wherein the second compound is a compound of Formula (VI), wherein each $X^1$ represents a $C_1$-$C_2$ alkyl group; $X^2$ and $X^3$ each independently represent a $C_1$-$C_2$ alkyl group or a $C_1$-$C_2$ alkoxy group; and each $X^4$ represents a $C_1$-$C_4$ alkylene group bonded to a nitrogen atom of the cyclic compound.

19. The method of claim 18, wherein the compound of Formula (VI) is tris(3-trimethoxysilylpropyl)isocyanurate.

20. The method of claim 1, wherein the aqueous mixture comprises a base and has a pH from about 8 to about 15.

21. The method of claim 20, wherein the base is ammonium hydroxide or a metal hydroxide.

22. The method of claim 1, wherein the aqueous mixture comprises an acid and has a pH from about 0.01 to about 6.0.

23. The method of claim 22, wherein the acid is an inorganic acid.

24. The method of claim 23, wherein the inorganic acid is hydrochloric acid.

25. The method of claim 1, wherein the slurry is aged in step (d) for up to 24 hours at a temperature of about 20° C. to about 125° C.

26. The method of claim 1, wherein the slurry is dried at a temperature of about 70° C. to about 150° C.

27. The method of claim 1, wherein step (c) is repeated one or more times to produce a thicker coating.

28. The method of claim 1, further comprising pre-treating the substrate.

29. The method of claim 28, wherein pre-treating the substrate comprises applying a solution comprising an oxidizing agent and an inorganic acid to the substrate.

30. The method of claim 29, wherein the oxidizing agent is hydrogen peroxide.

31. The method of claim 29, wherein the inorganic acid is sulfuric acid.

32. The method of claim 1, wherein the organosilica material has an average pore diameter of about 2.0 nm to about 25.0 nm.

33. The method of claim 1, wherein the organosilica material has a surface area of about 200 m$^2$/g to about 2500 m$^2$/g.

34. The method of claim 1, wherein the organosilica material has a pore volume of 0.1 cm$^3$/g about 3.0 cm$^3$/g.

35. The method of claim 1 further comprising agitating the slurry before coating.

36. The method of claim 1, wherein the adsorbent material is selected from the group consisting of a microporous adsorbent material, a mesoporous adsorbent material, an analogous periodic mesoporous adsorbent material, a metal oxide, a carbon, and a combination thereof.

37. The method of claim 1, wherein the adsorbent material is a zeolite.

38. The method of claim 37, wherein the zeolite is selected from the group consisting of a cationic form of zeolite A, Y, dealuminized Y, or Linde L; chabazite; erionite; mordenite; zeolite Beta; a ZSM-type zeolite; MCM-22; MCM-49; Nu-87; UTD-1; CIT-5; EMC-2; and Cloverite.

39. The method of claim 1, wherein the solution is stirred for at least 18 hours before adding the adsorbent material.

40. The method of claim 1, further comprising adding a $C_1$-$C_4$ alcohol to the solution.

41. The method of claim 39, wherein the $C_1$-$C_4$ alcohol is ethanol.

42. The method of claim 1, further comprising adding an additional amount of the compound of Formula (Ia) to the slurry.

43. The method of claim 42, wherein the compound of Formula (Ia) is 1,1,3,3,5,5-hexaethoxy-1,3,5-trisilacyclohexane.

44. The method of claim 1, further comprising supplying a purge gas to the substrate after coating.

45. The method of claim 44, wherein the purge gas is an inert gas.

46. The method of claim 45, wherein the inert gas is nitrogen.

47. The method of claim 1, wherein the substrate is selected from the group consisting of a capillary tube, a microchannel, a monolith, a spherical silica particle and a silicon wafer.

48. The method of claim 1, wherein the method does not comprise a calcination step.

49. The method of claim 1, wherein the coating has a thickness of up to about 150 μm.

50. The method of claim 48, wherein the coating comprises about 1% to about 50% organosilica material as a binder.

51. An organosilica material-coated substrate made according to claim 1.

52. A gas separation process comprising contacting a gas mixture comprising $CH_4$ and at least one contaminant selected from the group consisting $CO_2$, $H_2O$, $H_2S$, $NO_x$, and $SO_x$ with the organosilica material-coated substrate of claim 51.

53. The gas separation process of claim 52, wherein the process comprises PSA, TSA, PPSA, PTSA, RCPSA, RCTSA, RCPPSA or RCPTSA.

* * * * *